(12) United States Patent
Schnellmann et al.

(10) Patent No.: US 7,183,383 B2
(45) Date of Patent: Feb. 27, 2007

(54) USES OF COLLAGEN IV

(75) Inventors: Ricky Gene Schnellmann, Mount Pleasant, SC (US); Paul A. Nony, Little Rock, AR (US)

(73) Assignee: The University of Arkansas for Medical Sciences, Little Rock, AR (US)

( * ) Notice: Subject to any disclaimer, the term of this patent is extended or adjusted under 35 U.S.C. 154(b) by 496 days.

(21) Appl. No.: 10/393,193

(22) Filed: Mar. 20, 2003

(65) Prior Publication Data
US 2003/0181392 A1 Sep. 25, 2003

Related U.S. Application Data

(60) Provisional application No. 60/366,002, filed on Mar. 20, 2002, now abandoned.

(51) Int. Cl.
*A61K 38/17* (2006.01)
(52) U.S. Cl. ............... 530/356; 530/387.1; 514/21
(58) Field of Classification Search ......... 530/356, 530/387.1; 514/21
See application file for complete search history.

(56) References Cited

OTHER PUBLICATIONS

Nowak et al., Toxicology and Applied Pharmacology, vol. 167, pp. 37-45, 2000.*
Hudson et al., The Journal of Biological Chemistry, vol. 268, No. 35, pp. 26033-26036, Dec. 15, 1993.*
Kalluri et al., The Journal of Biological Chemistry, vol. 275, No. 17, pp. 12719-12724, Apr. 28, 2000.*
Houglum et al., Am. J. Clin. Nutr., vol. 54, pp. 1141S-1143S, 1991.*

* cited by examiner

*Primary Examiner*—Jon Weber
*Assistant Examiner*—Abdel A. Mohamed
(74) *Attorney, Agent, or Firm*—Benjamin Aaron Adles

(57) ABSTRACT

The present invention provides a method of recovering cellular functions in cells following injury, comprising the step of contacting said cells with collagen IV or a natural or mutated fragment thereof. Further provided is a pharmaceutical composition, comprising a therapeutically effective amount of collagen IV or a natural or mutated fragment thereof and a topically acceptable carrier.

4 Claims, 20 Drawing Sheets

USES OF COLLAGEN IV

CROSS-REFERENCE TO RELATED APPLICATION

This non-provisional patent application claims benefit of provisional patent application No. 60/366,002, filed Mar. 20, 2002, now abandoned.

FEDERAL FUNDING LEGEND

This invention was produced in part using funds obtained through a grant from the National Institute of Environmental Health Sciences grant NIH ES-O4410. Consequently, the federal government has certain rights in this invention.

BACKGROUND OF THE INVENTION

1. Field of the Invention

The present invention relates generally to the field of cellular injury. More specifically, the present invention relates to the uses of collagen IV in promoting recovery of cellular functions following cellular injury.

2. Description of the Related Art

The mesh-like basement membrane (BM) provides structural support and influences the growth, function, and survival of many cell types in most organ systems (15). Collagens are extracellular matrix (ECM) proteins that form the renal tubular basement membrane with other extracellular matrix proteins, such as laminin and heparan sulfate proteoglycans (29). The most abundant type of collagen in the basement membrane of the glomerulus and renal tubules is collagen IV, a globular, non-fibrillar protein. This characteristic distinguishes it from collagen I, the major fibrillar component of connective tissues and the second most abundant extracellular matrix protein in the proximal tubular basement membrane (12, 21).

Collagen IV forms a triple-helical monomer that consists most often of two $\alpha 1$(IV) chains and one $\alpha 2$(IV) chain or three $\alpha 1$(IV) chains (42,14). The collagen IV chains $\alpha 3$(IV), $\alpha 4$(IV), $\alpha 5$(IV), and $\alpha 6$(IV) have been identified and can associate in various combinations (15, 20). However, these isoforms have not been detected in the human proximal tubule or in primary cultures of rabbit renal proximal tubular cells (12, 29). Except in rodents, their renal expression appears to be limited to the distal tubular basement membrane and the glomerular basement membrane, where they have been implicated in the development of Goodpasture and Alport syndromes and diffuse leiomyomatosis (27, 29, 11, 15, 19, 20). Using functional analyses of cell-matrix interactions, collagen IV has been shown to play a crucial role in tubular function and kidney development (31). Because collagen IV is an important anchorage substrate for many cell types, especially in the kidney, the regulation of collagen IV synthesis and degradation plays an important role in cell function, growth, migration, and organ remodeling (15).

Under conditions of ischemia or after acute chemical exposures, renal epithelial cells may die or detach from the extracellular matrix and slough into the tubular lumen. Here they may aggregate with other sloughed cells, forming casts that cause tubular obstruction. Cells that do not die or become detached from the extracellular matrix are thought to dedifferentiate, proliferate, and migrate to denuded areas of the tubule, thus replacing the sloughed cells. The cells of the newly lined tubule may then differentiate, promoting the return of normal tubular function and overall renal function (1). The roles of collagens and other extracellular matrix proteins in renal cell survival, migration, and function have been examined (4). Surprisingly, few reports exist regarding the role of collagens in cellular repair and regeneration, although proliferation, migration, and return of normal functions do contribute to renal regeneration following injury (49).

Ascorbic acid is known to prevent the effects of scurvy, a disease characterized by defective connective tissue resulting from decreased collagen synthesis (40). In post-translational processing mechanisms, ascorbate acts as an essential iron reducing cofactor in the production of collagens, specifically in the hydroxylation of susceptible proline and lysine residues in procollagen $\alpha$ chains. These hydroxylation reactions are catalyzed by prolyl and lysyl hydroxylases, respectively, and are necessary for the proper folding of procollagen triple helices, as well as other post-translational modifications, including glycosylation and monomer crosslinking (9,24). Insufficiently hydroxylated procollagens have been shown to accumulate intracellularly, be deposited much more slowly, and be targeted for rapid degradation both intracellularly and extracellularly (17, 18, 42). Ascorbic acid also is known to promote the synthesis of both fibrillar and non-fibrillar collagen types in an array of cell types in vitro (10, 13, 33, 45). In addition, ascorbate has been suggested to act pretranslationally by stimulating mRNA expression of multiple collagen types in various culture systems, independent of its role as an enzymatic cofactor (6, 14, 32, 41, 46). Ascorbic acid has been implicated as an important mediator of cell growth and differentiation in a variety of cell types, through its effects on collagen synthesis and deposition (2). Through mechanisms unrelated to extracellular matrix production, ascorbic acid has been shown to both stimulate and inhibit cell proliferation depending on ascorbate concentration and cell type (48, 7, 16). Previous studies have demonstrated that ascorbic acid promotes increased cell growth and density, and improvement of key physiological functions including brush border enzyme activity, basal oxygen consumption, and $Na^+$-$K^+$-ATPase activity in primary cultures of rabbit renal proximal tubular cells (RPTC) (36).

The halocarbon conjugate S-(1,2-dichlorovinyl)-L-cysteine (DCVC) is a model toxicant that produces renal proximal tubular cell necrosis and acute renal failure (23). Primary cultures of rabbit renal proximal tubular cells sublethally injured by S-(1,2-dichlorovinyl)-L-cysteine neither proliferate nor repair physiological functions (38). In those experiments, renal proximal tubular cells were grown under physiological concentrations of all culture media supplements including 50 $\mu$M L-ascorbic acid 2-phosphate (AscP). However, upon addition of pharmacological concentrations of L-ascorbic acid 2-phosphate (500 $\mu$M), renal proximal tubular cells exposed to S-(1,2-dichlorovinyl)-L-cysteine were able to proliferate and repair physiological functions, although L-ascorbic acid 2 phosphate provided no protective effect during injury. In addition, pharmacological concentrations of ascorbic acid were shown to stimulate collagen IV synthesis and deposition in uninjured renal proximal tubular cells (39).

Cellular integrins are heterodimeric transmembrane receptors that provide a means for anchorage to extracellular substrates as well as two-way communication between the intracellular and the extracellular environments (Molitoris and Marrs, 1999; Ruoslahti and Engvall, 1997; Schoenwaelder and Burridge, 1999). Activation and clustering of integrins upon binding to extracellular matrix proteins initiate focal adhesion formation and the activation of cytoskeletal signaling cascades involved in cell growth, proliferation, migration, differentiation, and gene expression (Molitoris and Marrs, 1999; Schoenwaelder and Burridge, 1999, Zuk et al., 1998). In addition to binding to extracellular matrix substrates and mediating cytoskeletal signaling, integrins also are known to influence the formation and composition of the extracellular matrix (Gotwals, et al., 1996; Riikonen et al., 1995). In renal proximal tubular cells, integrins and other proteins, such as $Na^+/K^+$-ATPases, are localized to the basal membrane, where cells interact with the extracellular matrix as well as neighboring cells. These functions are in contrast to those of the apical membrane, where distinct physiological processes such as $Na^+$-dependent glucose and amino acid transport take place. The cellular polarity derived from the distinct functions carried out at separate membrane regions supports, and is critical for, proper renal tubular function (Bush et al., 2000).

The renal tubular basement membrane is composed mainly of collagens, laminins, and heparan sulfate proteoglycans (Furness, 1996, Miner, 1999). The most abundant type of collagen in the basement membrane of the glomerulus and renal tubules is collagen IV, a globular, non-fibrillar protein (Furness, 1996). The binding of integrins to collagens and other extracellular matrix proteins is determined largely by the combination of $\alpha$ and $\beta$ integrin subunits that form the functional heterodimer. At least eight $\beta$ subunits and 17 $\alpha$ subunits have been identified to date, and they associate non-covalently to form more than 20 heterodimers with various signaling and substrate binding properties (Kreidberg and Symons, 2000). Cells most often utilize the integrin heterodimers $\alpha_1\beta_1$ and $\alpha_2\beta_1$ to bind collagen IV, and the importance of signals derived from collagen-binding integrins (CBIs) in normal cellular activities have been studied (Gardner et al., 1996; Knight et al., 1998; Kuhn and Ebel, 1994).

In cases of acute renal failure resulting from chemical exposure or ischemia, tubular epithelial cells may lose polarity, as characterized by decreased localization of integrins in the basal membrane and their redistribution throughout the plasma membrane (Goligorsky and DiBona, 1993; Lieberthal et al., 1997;

Molitoris and Marrs, 1999; Zuk et al., 1998). Loss of cellular polarity results in cellular disorientation, decreased renal tubular function, and cell death and/or detachment from the tubular basement membrane (Frisch and Ruoslahti, 1997; Goligorsky and DiBona, 1993; Molitoris and Marrs, 1999; Tang et al., 1998). Sublethally injured cells that do not die or become detached from the basement membrane are thought to repair and/or dedifferentiate, proliferate, migrate to denuded areas of the tubule, differentiate, and promote the return of normal renal function (Abbate and Remuzzi, 1996; Molitoris and Marrs, 1999). The effects of cell injury on integrin localization and renal cell polarity have been investigated, but their importance in tubular regeneration following injury is not well understood (Goligorsky and DiBona, 1993; Lieberthal et al., 1997; Kreidberg and Symons, 2000; Molitoris and Marrs, 1999; Zuk et al, 1998).

Studies have examined the mechanisms of renal tubular cell regeneration using the model nephrotoxicant S-(1,2-dichlorovinyl)-L-cysteine to produce sublethal injury in primary cultures of rabbit renal proximal tubular cells. Exposure to S-(1,2-dichlorovinyl)-L-cysteine to produce approximately 50% cell death and loss caused the irreversible inhibition of key physiological functions, including mitochondrial function, active $Na^+$ transport, and $Na^+/K^+$-ATPase activity in the remaining sublethally-injured renal proximal tubular cells (Nowak et al., 1999). However, addition to the culture media of L-ascorbic acid-2-phosphate at pharmacological concentrations promoted proliferation and repair of physiological functions in S-(1,2-dichlorovinyl)-L-cysteine-injured renal proximal tubular cells (Nowak et al., 2000).

Thus, the prior art is deficient in novel uses of collagen IV. The present invention fulfills this long-standing need and desire in the art.

SUMMARY OF THE INVENTION

Collagen IV is found in the renal proximal tubular cell basement membrane and is a mediator of renal development and function. Pharmacological concentrations of L-ascorbic acid phosphate (AscP) promote the repair of physiological functions in renal proximal tubular cells sublethally injured by S-(1,2-dichlorovinyl)-L-cysteine. AscP promotes renal proximal tubular cell repair by stimulating collagen IV synthesis and/or deposition. Renal proximal tubular cells exhibit increased synthesis but decreased deposition of collagen IV following S-(1,2-dichlorovinyl)-L-cysteine exposure. In contrast, renal proximal tubular cells cultured in pharmacological concentrations of AscP maintain collagen IV deposition. The activity of prolyl hydroxylase is decreased in renal proximal tubular cells after S-(1,2-dichlorovinyl)-L-cysteine injury, an effect that is partially attenuated in injured renal proximal tubular cells cultured in pharmacological concentrations of AscP. The addition of exogenous collagen IV to the culture media of S-(1,2-dichlorovinyl)-L-cysteine-injured renal proximal tubular cells promotes the repair of mitochondrial function and $Na^+/K^+$-ATPase activity. However, neither collagen I, laminin, nor fibronectin promotes cell repair. These data demonstrate an association between AscP-stimulated deposition of collagen IV and exogenous collagen IV and repair of physiological functions, suggesting that collagen IV plays a specific role in renal proximal tubular cells repair following sublethal injury.

Thus, collagen IV selectively promotes the repair of physiological processes in sublethally injured renal proximal tubular cells. The mechanisms of cell repair were examined by measuring the effects of toxicant injury and stimulation of repair by L-ascorbic acid-2-phosphate, exogenous collagen IV, or function-stimulating integrin antibodies on the expression and subcellular localization of collagen-binding integrins (CBI) in renal proximal tubular cells. Expression of CBI subunits $\alpha_1$, $\alpha_2$, and $\beta_1$ in renal proximal tubular cells was not altered on day 1 after sublethal injury by S-(1,2-dichlorovinyl)-L-cysteine. On day 6, expression of $\alpha_1$ and $\beta_1$ subunits remained unchanged, while a 2.2-fold increase in $\alpha_2$ expression was evident in injured renal proximal tubular cells. CBI localization in control renal proximal tubular cells was limited exclusively to the basal membrane. On day 1 following injury, renal proximal tubular cells exhibited a marked inhibition of active $Na^+$ transport and a loss of cell polarity, characterized by a decrease in basal CBI localization and the appearance of CBIs on the apical membrane. On day 6 after injury, renal proximal tubular cells still exhibited marked inhibition of active $Na^+$ transport and localization of collagen binding integrins to the apical membrane. However, S-(1,2-dichlorovinyl)-L-cysteine-injured renal proximal tubular cells cultured in pharmacological concentrations of AscP (500 μM) or exogenous collagen IV (50 μg/ml) exhibited an increase in active $Na^+$ transport, relocalization of collagen binding integrins to the basal membrane, and the disappearance of collagen binding integrins from the apical membrane on day 6. Function-stimulating antibodies to collagen binding $\beta_1$ integrins did not promote basal relocalization of collagen binding integrins despite the stimulation of the repair of $Na^+/K^+$-ATPase activity on day 6 after injury.

These data demonstrate that S-(1,2-dichlorovinyl)-L-cysteine disrupts integrin localization, and that physiological repair stimulated by AscP or collagen IV is associated with the basal relocalization of collagen binding integrins in S-(1,2-dichlorovinyl)-L-cysteine-injured renal proximal tubular cells. These data also suggest that CBI-mediated repair of physiological functions may occur independently of integrin relocalization.

It is an object of the present invention to examine the effect of S-(1,2-dichlorovinyl)-L-cysteine on the synthesis, deposition, and proline hydroxylation of collagen IV in S-(1,2-dichlorovinyl)-L-cysteine-injured renal proximal tubular cells; 2) to determine if AscP-stimulated synthesis and/or deposition of collagen IV is associated with AscP-stimulated repair of physiological functions in S-(1,2-dichlorovinyl)-L-cysteine-injured renal proximal tubular cells; and 3) to characterize the specific role of collagen IV and other extracellular matrix proteins in renal proximal tubular cell repair.

Based on these findings, it appears that L-ascorbic acid-2-phosphate and exogenous collagen IV act to promote renal proximal tubular cell regeneration through the restoration of interactions between collagen IV and CBI. Other objects of the present invention include 1) to determine the fate of collagen binding integrins following sublethal renal proximal tubular cells injury with regards to expression and subcellular localization; and 2) to examine the effect of L-ascorbic acid-2-phosphate, exogenous collagen IV, and function-stimulating CBI antibodies on CBI expression and/or localization following sublethal injury in relation to the repair of physiological functions.

In one embodiment of the present invention, there is provided a method of recovering cellular functions in cells following injury, comprising the step of contacting said cells with collagen IV or a natural or mutated fragment thereof.

In another embodiment of the present invention, there is provided a pharmaceutical composition, comprising a therapeutically effective amount of collagen IV or a natural or mutated fragment thereof and a pharmaceutically acceptable carrier.

In yet another embodiment of the present invention, there is provided a method of recovering cellular functions following injury in an individual in need of such treatment, comprising the step of administering a therapeutically effective amount of the pharmaceutical composition of the present invention to the individual.

In yet another embodiment of the present invention, there is provided a method of recovering cellular functions in cells following injury, comprising the step of stimulating the collagen IV receptor in the cells.

Other and further aspects, features, and advantages of the present invention will be apparent from the following description of the presently preferred embodiments of the invention. These embodiments are given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIG. 15A, control renal proximal tubular cells; FIG. 15E, sub-confluent control renal proximal tubular cells; FIGS. 15B and 15F, S-(1,2-dichlorovinyl)-L-cysteine-injured renal proximal tubular cells; FIGS. 15C and 15G, S-(1,2-dichlorovinyl)-L-cysteine-injured renal proximal tubular cells cultured in the presence of pharmacological concentrations of L-ascorbic acid-2-phosphate; FIGS. 15D and 15H, S-(1,2-dichlorovinyl)-L-cysteine-injured renal proximal tubular cells cultured in the presence of exogenous collagen IV. Shown are representative confocal photomicrographs from 3–4 separate experiments (magnification=400×).

(FIGS. 16A–16D) and day 6 (FIGS. 16E–16H) after S-(1,2-dichlorovinyl)-L-cysteine exposure. FIG. 16A, control renal proximal tubular cells; FIG. 16E, sub-confluent control renal proximal tubular cells; FIGS. B and F, S-(1,2-dichlorovinyl)-L-cysteine-injured renal proximal tubular cells; FIGS. C and G, S-(1,2-dichlorovinyl)-L-cysteine-injured renal proximal tubular cells cultured in the presence of pharmacological concentrations of L-ascorbic acid-2-phosphate; FIGS. D and H, DCVC-injured renal proximal tubular cells cultured in the presence of exogenous collagen IV. Shown are representative photomicrographs from 3–4 separate experiments (magnification=400×).

FIG. 17A, control renal proximal tubular cells; FIG. 17E, sub-confluent control RPTC; FIGS. B and F, S-(1,2-dichlorovinyl)-L-cysteine-injured renal proximal tubular cells; FIGS. C and G, S-(1,2-dichlorovinyl)-L-cysteine-injured renal proximal tubular cells cultured in the presence of pharmacological concentrations of L-ascorbic acid-2-phosphate; Q FIGS. D and H, S-(1,2-dichlorovinyl)-L-cysteine-injured renal proximal tubular cells cultured in the presence of exogenous collagen IV. Shown are representative confocal photomicrographs from 3–4 separate experiments (magnification=400×).

FIG. 18A, control renal proximal tubular cells; FIG. 18E, sub-confluent control RPTC; FIGS. B and F, S-(1,2-dichlorovinyl)-L-cysteine-injured renal proximal tubular cells; FIGS. C and G, S-(1,2-dichlorovinyl)-L-cysteine-injured renal proximal tubular cells cultured in the presence of pharmacological concentrations of L-ascorbic acid-2-phosphate; FIGS. D and H, S-(1,2-dichlorovinyl)-L-cysteine-injured renal proximal tubular cells cultured in the presence of exogenous collagen IV. Shown are representative photomicrographs from 3–4 separate experiments (magnification=400×).

FIG. 19A, control renal proximal tubular cells; FIG. 19E, sub-confluent control renal proximal tubular cells; FIGS. 19B and 19F, S-(1,2-dichlorovinyl)-L-cysteine-injured renal proximal tubular cells; FIGS. 19C and 19G, S-(1,2-dichlorovinyl)-L-cysteine-injured renal proximal tubular cells cultured in the presence of pharmacological concentrations of L-ascorbic acid-2-phosphate; FIGS. 19D and 19H, S-(1,2-dichlorovinyl)-L-cysteine-injured renal proximal tubular cells cultured in the presence of exogenous collagen IV. Shown are representative confocal photomicrographs from 3–4 separate experiments (magnification=400×).

FIG. 20A, control renal proximal tubular cells; FIG. 20E, sub-confluent control renal proximal tubular cells; FIGS. 20B and 20F, S-(1,2-dichlorovinyl)-L-cysteine-injured renal proximal tubular cells; FIGS. 20C and 20G, S-(1,2-dichlorovinyl)-L-cysteine-injured renal proximal tubular cells cultured in the presence of pharmacological concentrations of L-ascorbic acid-2-phosphate; FIGS. 20D and 20H, S-(1,2-dichlorovinyl)-L-cysteine-injured renal proximal tubular cells cultured in the presence of exogenous collagen IV. Shown are representative photomicrographs from 3–4 separate experiments (magnification=400×).

FIGS. 22A and 22D, control renal proximal tubular cells; FIGS. 22B and 22E, S-(1,2-dichlorovinyl)-L-cysteine-injured renal proximal tubular cells; FIGS. 22C and 22F, S-(1,2-dichlorovinyl)-L-cysteine-injured renal proximal tubular cells $\beta_1$-stimulating antibody. Shown are representative confocal photomicrographs from 2 separate experiments (magnification=400×).

DETAILED DESCRIPTION OF THE INVENTION

Figure 1:
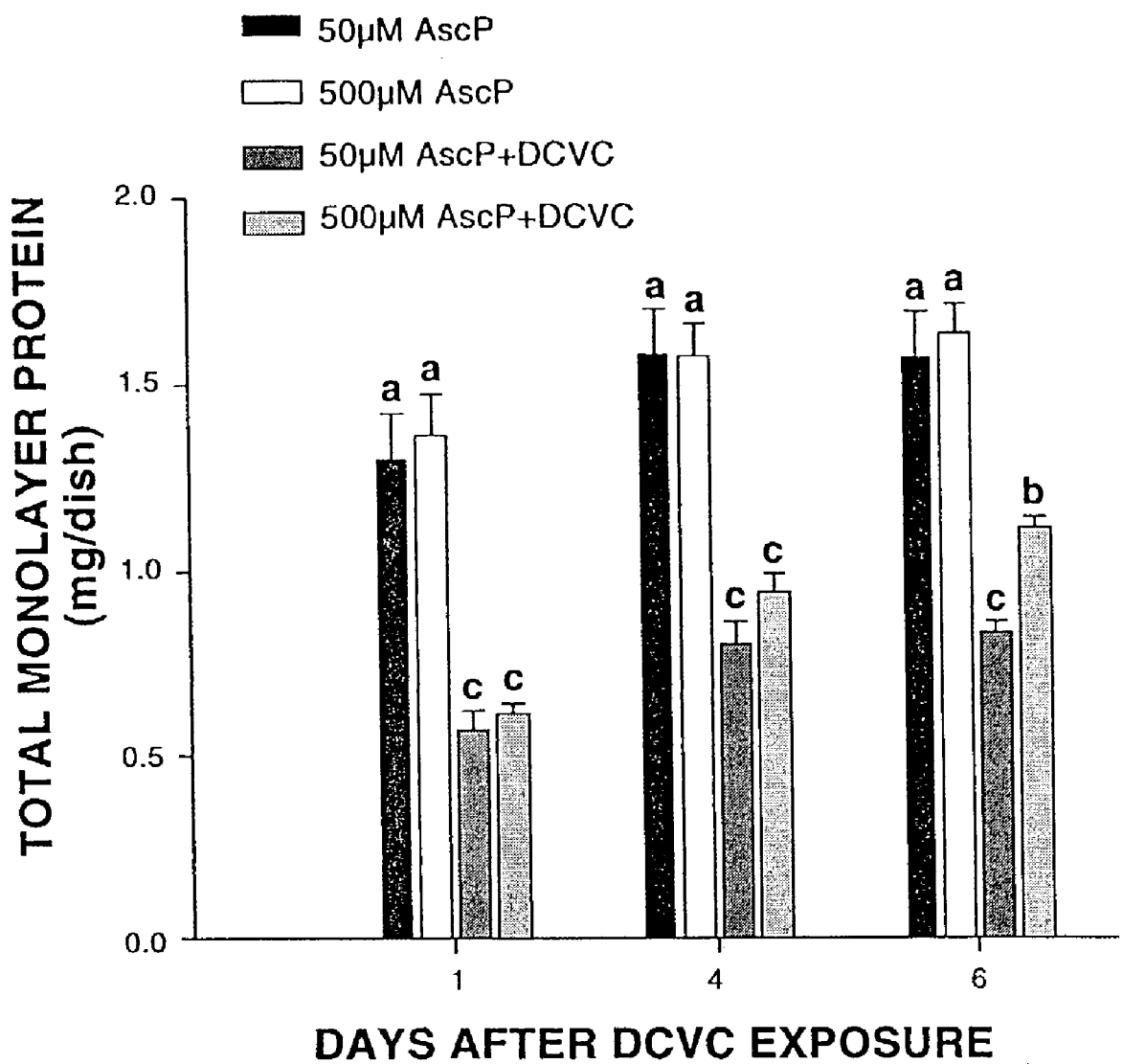
FIG. 1 shows the total protein content over time in renal proximal tubular cells sublethally injured by S-(1,2-dichlorovinyl)-L-cysteine in the presence of 50 μM or 500 μM L-ascorbic acid-2-phosphate. Renal proximal tubular cells were exposed to S-(1,2-dichlorovinyl)-L-cysteine (200 μM) for 1.75 hours, and protein content was measured on days 1, 4, and 6 following injury. Data are presented as means±SEM, n=5 separate experiments. Bars labeled with different letter symbols are significantly different from each other (P<0.05).

The present invention is directed to a method of recovering cellular functions in cells following injury, comprising the step of contacting said cells with collagen IV or a natural or mutated fragment thereof. Generally, the concentration of said collagen IV is from about 0.01 mM to about 100 mM. Generally, the injury is selected from the group consisting of ischemic injury, drug induced injury and a toxicant induced injury. Representative injuries include, but are not limited to, drug-induced intestine injury, toxicant-induced intestinal injury, ischemic reperfusion injury of the intestine, ischemic bowel disease, drug-induced liver injury, toxicant-induced liver injury, ischemic/reperfusion injury of the liver, acute liver failure, drug-induced lung injury, toxicant-induced lung injury, ischemic reperfusion injury of the lung, acute lung failure, drug-induced heart injury, toxicant-induced heart injury, ischemic/reperfusion injury of the heart, acute heart failure, drug-induced brain injury, toxicant-induced brain injury, ischemic reperfusion injury of the brain, stroke, drug-induced kidney injury, toxicant-induced kidney injury, ischemic reperfusion injury of the kidney, acute renal failure, drug-induced eye injury, toxicant-induced eye injury, ischemic reperfusion injury of the eye, chronic liver failure, chronic renal failure and vascular injury.

The present invention is directed to a pharmaceutical composition, comprising a therapeutically effective amount of collagen IV or a natural or mutated fragment thereof and a pharmaceutically acceptable carrier.

The present invention is further directed to a method of recovering cellular functions following injury in an individual in need of such treatment, comprising the step of administering a therapeutically effective amount of the pharmaceutical composition of the present invention to the individual. Generally, the concentration of said collagen IV is from about 0.01 mg/kg to about 100 mg/kg. Representative injuries which may be treated using this pharmaceutical composition are described above.

The present invention is directed to a method of recovering cellular functions in cells following injury, comprising the step of stimulating the collagen IV receptor in said cells. Representative injuries which may be treated using this method are described above. A person having ordinary skill in this art would readily appreciate that the collagen IV receptor could be stimulated using a variety of means. Representative examples of techniques to stimulate the collagen IV receptor include using a collagen IV antibody, a collagen IV antibody fragment or a collagen IV receptormimetic.

A person having ordinary skill in this art would readily recognize that one could use not only collagen IV in the methods and compositions of the present invention but also any smaller peptide fragment of collagen IV that exhibits the same activity. Further, a person having ordinary skill in this art could readily design a peptide fragment using non-natural amino acids that exhibit the same activity as in the parent collagen IV.

It is specifically contemplated that pharmaceutical compositions may be prepared using a pharmacological concentration of collagen IV disclosed in the present invention. It is not intended that the present invention be limited by the particular nature of the therapeutic preparation, so long as the preparation comprises collagen IV or fragments or analogs thereof. These therapeutic preparations can be administered to mammals for veterinary use, such as with domestic animals, and clinical use in humans in a manner similar to other therapeutic agents. In general, the dosage required for therapeutic efficacy will vary according to the type of use and mode of administration, as well as the particularized requirements of individual hosts. A person having ordinary skill in this art would readily be able to determine, without undue experimentation, the appropriate dosages and routes of administration of the collagen IV or fragments or analogs thereof of the present invention.

The following examples are given for the purpose of illustrating various embodiments of the invention and are not meant to limit the present invention in any fashion.

EXAMPLE 1

Materials

Female New Zealand White rabbits (1.5–2.0 kg) were purchased from Myrtle's Rabbitry (Thompson Station, Tenn.). S-(1,2-dichlorovinyl)-L-cysteine was a gift from Dr. T. W. Petry (Pharmacia Upjohn, Kalamazoo, Mich.) and was synthesized as previously described (30). L-Ascorbic acid-2-phosphate (magnesium salt) was purchased from Wako Chemicals USA, Inc. (Richmond, Va.). Ouabain was obtained from RBI/Sigma (Natick, Mass.). [$^{35}$S]-L-Methionine (>1000 Ci/mmol) was purchased from ICN Biomedicals (Costa Mesa, Calif.). [$^{14}$C]-L-Proline (0.275 Ci/mmol) and 4-[$^3$H]-L-proline (24 Ci/mmol) were purchased from New England Nuclear Life Science Products (Boston, Mass.). The mouse anti-collagen IV monoclonal antibody M3F7, developed by Dr. Heinz Furthmayr, was obtained from the Developmental Studies Hybridoma Bank (University of Iowa, Iowa City, Iowa). Hyperfilm ECL was purchased from Amersham Life Science (Cleveland, Ohio). Hyamine hydroxide was purchased from ICN Radiochemicals (Irvine, Calif.). Rat tail collagen I was purchased from Collaborative Biochemical Products (Bedford, Mass.). Human cellular fibronectin was purchased from Upstate Biotech (Lake Placid, N.Y.). Human placenta collagen IV, laminin, and all other materials were purchased from Sigma Chemical Co. (St. Louis, Mo.).

EXAMPLE 2

Isolation of Proximal Tubules and Culture Conditions

Rabbit renal proximal tubules were isolated using the iron oxide perfusion method and grown in 35-mm tissue culture dishes or 48-well cell culture clusters under improved conditions as previously described (35, 36). The cell culture medium was a 1:1 mixture of DMEM/Ham's F-12 (without D-glucose, phenol red, or sodium pyruvate) supplemented with 15 mM HEPES buffer, 2.5 mM L-glutamine, 1 μM pyridoxine HCl, 15 mM sodium bicarbonate, and 6 mM lactate. Hydrocortisone (50 nM), selenium (5 ng/ml), human transferrin (5 μg/ml), bovine insulin (10 nM), and L-ascorbic acid-2-phosphate (50 μM or 500 μM) were added to fresh culture medium immediately prior to daily media change. L-Ascorbic acid-2-phosphate (AscP) was used due to the fact that L-ascorbic acid is unstable in culture media. AscP is stable in culture media for ≧7 days at 37° C. and, after intracellular dephosphorylation, has the same effect on cultured cells as L-ascorbic acid (13).

EXAMPLE 3

Sublethal Injury of RPTC

Confluent monolayers of renal proximal tubular cells (day 6 after seeding) were exposed to 200 μM S-(1,2-dichlorovinyl)-L-cysteine (dissolved in water) for 1.75 hours followed by toxicant removal and addition of fresh culture media. This method produces approximately 50% cell death and loss 24 hours after the exposure. On days 1, 4, and 6 following S-(1,2-dichlorovinyl)-L-cysteine exposure, the ability of the remaining renal proximal tubular cells to regenerate and repair physiological function was monitored as described below. In some experiments, immediately after S-(1,2-dichlorovinyl)-L-cysteine exposure and after daily media change through day 6 after injury, collagen I (0, 5, 15, or 50 μg/ml), collagen IV (0, 5, 15, or 50 μg/ml), laminin (50 μg/ml), or cellular fibronectin (50 μg/ml) was added to the culture media of uninjured and S-(1,2-dichlorovinyl)-L-cysteine-injured renal proximal tubular cells grown in physiological concentrations of AscP. Exogenous collagens I and IV used in this study were triple helical and contained only α1 and α2 chains in conformations similar to those found in the renal basement membrane (3, 25). Laminin was a mixture of biologically active laminin chains found in most epithelial tissues (8, 50) and cellular fibronectin was composed of functional dimers (51).

EXAMPLE 4

Cell Density

Measurement of monolayer protein content over time was used to estimate cell density. On days 1, 4, and 6 after sublethal S-(1,2-dichlorovinyl)-L-cysteine injury, renal proximal tubular cell monolayers were washed with PBS and solubilized in Triton buffer (0.05% Triton X-100, 100 mM Tris-Base, 150 mM NaCl, pH 7.5). Samples were sonicated and protein concentrations determined using the method of Lowry (26) or the bicinchoninic acid microassay according to the manufacturer's instructions (Pierce, Rockford, Ill.).

EXAMPLE 5

Basal Oxygen Consumption ($QO_2$)

On days 1, 4, and 6 after sublethal S-(1,2-dichlorovinyl) L-cysteine injury, renal proximal tubular cells bathed in 37° C. culture medium were gently detached from culture dishes with a rubber policeman and transferred to a 37° C. oxygen consumption ($QO_2$) chamber. Basal renal proximal tubular cells $QO_2$ was measured polarographically using a Clark-type electrode as described previously (36).

EXAMPLE 6

Na$^+$/K$^+$-ATPase Activity

On days 1 and 6 after sublethal S-(1,2-dichlorovinyl)-L-cysteine injury, total ATPase activity was measured using a modification of a previously described procedure (44). Briefly, renal proximal tubular cells cultured in 48-well cell culture clusters were scraped and incubated in dissociation buffer (5 mM HEPES (pH 7.4), 25 mM imidazole, 1% BSA, 0.065% sodium dodecyl sulfate (SDS)) for 10 min. at room temperature and placed on ice. The dissociated renal proximal tubular cells were then diluted 5-fold with additional dissociation buffer minus SDS. Aliquots of dissociated renal proximal tubular cells were combined with fresh ATPase assay buffer (2.54 mM MgCl$_2$, 100 mM NaCl, 10 mM KCl, 5 mM HEPES, 10 U/ml lactate dehydrogenase, 7 U/ml pyruvate kinase, 2.54 mM Na$_2$ATP, 2.54 mM phospho(enol)pyruvate, and 0.5 mM β-NADH). ATPase activity was measured under linear conditions spectrophotometrically as the oxidation of β-NADH to NAD$^+$ at 37° C. in the absence or presence of ouabain (0.1 mM) at a wavelength of 340 nm. Na$^+$/K$^+$-ATPase activity was calculated as total ATPase activity minus ouabain-insensitive ATPase activity.

EXAMPLE 7

Immunoprecipitation of Synthesized and Deposited Collagen IV

Immunoprecipitation of newly synthesized and deposited collagen IV was performed using the method of Niki et al., with some modifications (34). On days 1, 4, and 6 after sublethal S-(1,2-dichlorovinyl)-L-cysteine injury, renal proximal tubular cells were metabolically labeled for 24 hours with 25 μCi/ml of [$^{35}$S]-L-methionine. Cell monolayers were washed with PBS, solubilized for 30 minutes in lysis buffer (20 mM Tris-HCl (pH 8.8), 2 mM EDTA, 0.2 mM PMSF, 10 mM N-ethylmaleimide, 1% Triton X-100, 1% sodium deoxycholic acid, 150 mM NaCl, and 1 mM EGTA) containing protease inhibitors (25 μg/ml pepstatin A, 12.5 μg/ml leupeptin, 12.5 μg/ml aprotinin), and centrifuged at 15,000×g for 10 minutes at 4° C. The resulting supernatants (soluble fraction, cell-associated collagen) were transferred to fresh tubes, snap frozen in liquid N$_2$, and stored at −80° C. Pelleted material (insoluble fraction, ECM-associated collagen) was resuspended in pellet solubilization buffer (20 mM Tris-HCl (pH 8.8), 2 mM EDTA, 0.2 mM PMSF, 10 mM N-ethylmaleimide, 1% sodium dodecyl sulfate, and 10 mM dithiothreitol), sonicated, boiled for 5 minutes, and incubated in the presence of iodoacetamide (25 mM) for 30 minutes at 37° C. with shaking. Samples were centrifuged at 15,000×g for 10 minutes at 4° C. Supernatants were then transferred to fresh microcentrifuge tubes, snap frozen in liquid N$_2$, and stored at −80° C. Protein concentration in cell-associated and ECM-associated fractions was determined using a Coomassie protein microassay (Pierce, Rockford, Ill.) with BSA as the standard. Sample aliquots equaling 0.5 mg of total protein were diluted 3-fold in immunoprecipitation buffer (20 mM Tris-HCl (pH 8.8), 2 mM EDTA, 0.2 mM PMSF, 10 mM N-ethylmaleimide) and precleared with 20 μl (50% slurry) of Protein G-agarose beads for 2 hours. Samples were then incubated overnight with 0.05 mg of an anti-collagen IV monoclonal antibody (clone M3F7) at 4° C. with vigorous shaking. Samples were incubated for 2 hours at 4° C. with shaking in the presence of goat anti-mouse IgG at a concentration in two-fold excess of that of the primary antibody. Immune complexes were precipitated for 2 hours at 4° C. with shaking using 40 μl (50% slurry) of Protein G-agarose beads.

To collect the collagen IV immune complexes, samples were centrifuged at 15,000×g for 1 minute at 4° C. The supernatant was aspirated, and the pelleted beads washed with washing buffer (20 mM Tris-HCl (pH 8.8), 2 mM EDTA, 0.5 M NaCl, 0.5% sodium deoxycholic acid, 0.5% Triton X-100, 0.1% sodium dodecyl sulfate, and 0.1% bovine serum albumin) and centrifuged for 1 minute at 15,000×g at 4° C. This was repeated twice using distilled water in the final wash. Reducing sample buffer (1 M Tris-HCl, pH 6.8, 10% glycerol, 10% sodium dodecyl sulfate, 0.2% bromophenol blue, and 5% 2-mercaptoethanol) was added to each sample just prior to boiling for 10 minutes to release the collagen IV from the immune complexes. After boiling, samples were centrifuged for 1 minute at 15,000×g at 4° C., snap frozen in liquid N$_2$, and stored at −80° C. until further use.

EXAMPLE 8

SDS-PAGE and Autoradiography

Radiolabeled collagen IV was separated by SDS-PAGE and visualized by autoradiography (22). Each radiolabeled collagen IV immunoprecipitate (20 μl) was subjected to electrophoresis and the gels stained, dried, and exposed to film for 3 weeks at −80° C. After film development, densitometry of the resulting 206 kDa bands was calculated using NIH Image software.

EXAMPLE 9

Proline Hydroxylation in Newly Synthesized Collagen IV

Proline hydroxylation in collagen molecules occurs at the 4-trans position. Therefore, the extent of proline hydroxylation can be estimated by the loss of hydrogen from the 4-trans position of proline in the hydroxylation reaction. A previously described dual-labeling technique for the determination of proline hydroxylation was modified using [$^{14}$C]-L-proline and 4-[$^3$H]-L-proline incorporation into collagen IV and measuring the ratio of [$^3$H]:[$^{14}$C] in collagen IV molecules (5). A greater extent of proline hydroxylation at the 4-trans position of proline will result in a decrease in the ratio of [$^3$H]:[$^{14}$C] in newly synthesized collagen molecules due to the loss of [$^3$H]. Renal proximal tubular cells were dual-labeled for 24 hours with [$^{14}$C]-L-proline (15 RCi/ml) and 4-[$^3$H]-L-proline (62.5 μCi/ml) immediately after S-(1, 2-dichlorovinyl)-L-cysteine exposure. Cell-associated and deposited proteins were harvested, and collagen IV was immunoprecipitated as described above. Immunoprecipitated collagen IV was visualized by SDS-PAGE as described above, the 206 kDa bands in the destained gels were excised, and the protein was extracted with 90% hyamine hydroxide overnight at 37° C. [$^{14}$C]-Proline and 4-[$^3$H]-proline in collagen IV was determined using liquid scintillation spectrometry, and the extent of proline hydroxylation was calculated as the ratio of [$^3$H]:[$^{14}$C].

EXAMPLE 10

Statistical Analysis

Renal proximal tubular cells isolated from one rabbit represent one experiment (n=1) that consisted of data collected from 2–6 plates of cells. Experiments were repeated until an n of 3–5 was reached. Data are presented as means±SEM. Significant differences between treatment groups (p<0.05) were determined using SigmaStat one-way ANOVA or two-way ANOVA as necessary and Student-Newman-Keuls tests for the comparison of multiple means (Jandel Scientific, San Rafael, Calif.).

EXAMPLE 11

Cell Density

Monolayer protein content was used to measure cell density over a 6-day recovery period in renal proximal tubular cells sublethally injured by S-(1,2-dichlorovinyl)-L-cysteine. There were no significant differences at any time point in monolayer protein content between untreated renal proximal tubular cells grown in 50 μM or 500 μM AscP. One day after DCVC exposure (200 μM), renal proximal tubular cells cultured in 50 μM AscP exhibited a 56% decrease in monolayer protein content compared to control, representing cell death and loss (FIG. 1). Renal proximal tubular cells cultured in the presence of 500 μM L-ascorbic acid-2-phosphate sustained the same degree of cell death and loss (55%) on day 1. Monolayer protein content 4 days following S-(1,2-dichlorovinyl)-L-cysteine exposure remained at day 1 levels in renal proximal tubular cells incubated in 50 μM or 500 μM L-ascorbic acid-2-phosphate. However, 6 days after S-(1,2-dichlorovinyl)-L-cysteine exposure, monolayer protein content in S-(1,2-dichlorovinyl)-L-cysteine-treated renal proximal tubular cells that were cultured in 500 μM L-ascorbic acid-2-phosphate was 34% greater than that of S-(1,2-dichlorovinyl)-L-cysteine-treated renal proximal tubular cells grown in 50 μM AscP. These data show that pharmacological concentrations of ascorbic acid do not protect against S-(1,2-dichlorovinyl)-L-cysteine-induced cell injury and loss but do promote an increase in cell density over time in renal proximal tubular cells sublethally injured by S-(1,2-dichlorovinyl)-L-cysteine.

EXAMPLE 12

Basal $QO_2$ and $Na^+/K^+$-ATPase Activity

Figure 2A:
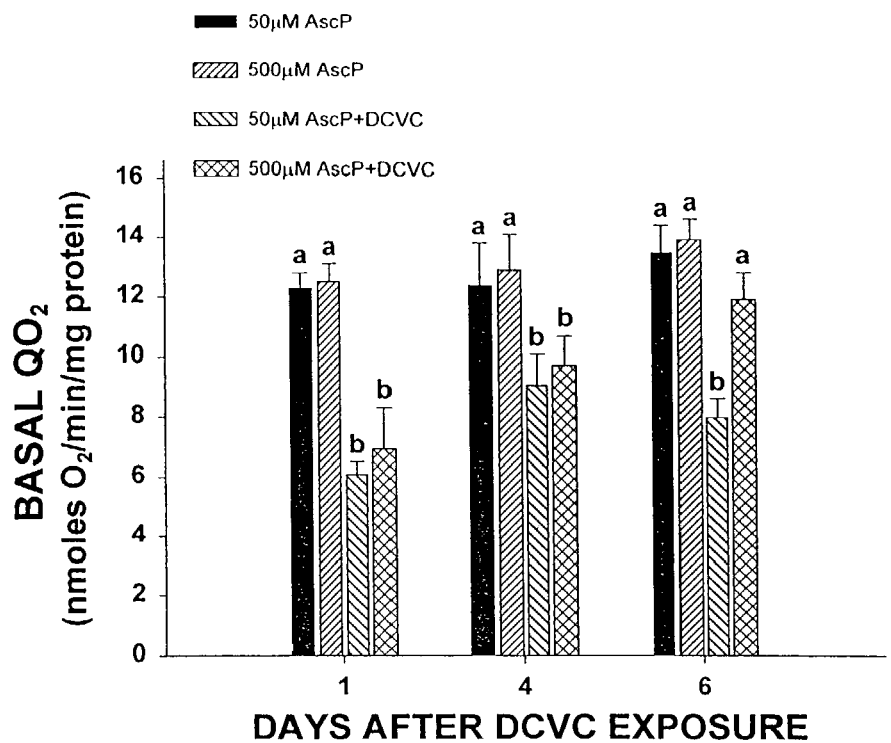
FIGS. 2A–2B show the basal oxygen consumption ($QO_2$, FIG. 2A) and $Na^+/K^+$-ATPase activity (FIG. 2B) in renal proximal tubular cells sublethally injured by S-(1,2-dichlorovinyl)-L-cysteine in the presence of either 50 μM or 500 μM AscP. Renal proximal tubular cells were exposed to DCVC (200 μM) for 1.75 hours. $QO_2$ was measured on days 1, 4, and 6 following injury, and $Na^+/K^+$-ATPase activity was measured on days 1 and 6 after injury. Data are presented as means ±SEM, n=3–5 separate experiments. Bars labeled with different letter symbols are significantly different from each other (P<0.05).
Figure 2B:
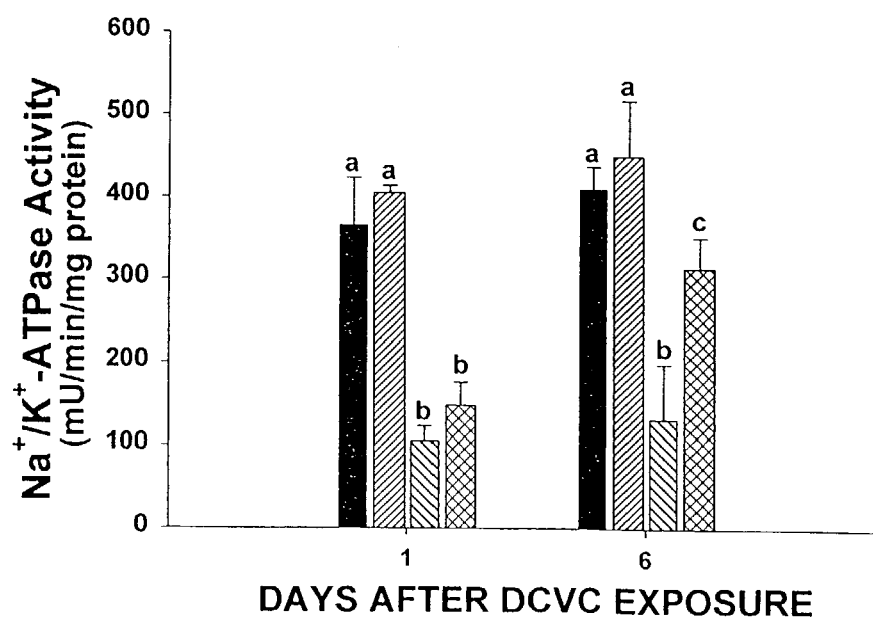

Basal $QO_2$ (a measure of mitochondrial function) and $Na^+/K^+$-ATPase activity were used as measures of physiological functions in renal proximal tubular cells over the 6 day recovery period following S-(1,2-dichlorovinyl)-L-cysteine exposure. Basal $QO_2$ and $Na^+/K^+$-ATPase activity in untreated renal proximal tubular cells grown in 50 μM and 500 μM L-ascorbic acid-2-phosphate were equivalent at all time points. One day after S-(1,2-dichlorovinyl)-L-cysteine exposure (200 μM), renal proximal tubular cells grown in both 50 μM and 500 μM AscP exhibited decreases in $QO_2$ and $Na^+/K^+$-ATPase activity of approximately 50% and 65% (FIGS. 2A and 2B, respectively). $QO_2$ remained at day 1 levels on day 4 after S-(1,2-dichlorovinyl)-L-cysteine exposure in renal proximal tubular cells incubated in 50 μM or 500 μM L-ascorbic acid-2-phosphate. On day 6, $QO_2$ in renal proximal tubular cells grown in 500 μM L-ascorbic acid-2-phosphate was 49% higher than that in renal proximal tubular cells grown in 50 μM AscP and equal to that of controls. Similarly, $Na^+/K^+$-ATPase activity on day 6 was approximately 150% higher in S-(1,2-dichlorovinyl)-L-cysteine-injured renal proximal tubular cells cultured in 500 μM L-ascorbic acid-2-phosphate than in injured renal proximal tubular cells cultured in physiological concentrations of L-ascorbic acid-2-phosphate. These data show that pharmacological concentrations of ascorbic acid do not prevent the inhibition of physiological functions caused by DCVC exposure but do stimulate physiological repair in renal proximal tubular cells sublethally injured by S-(1,2-dichlorovinyl)-L-cysteine.

EXAMPLE 13

Synthesis of Collagen IV

Figure 3:
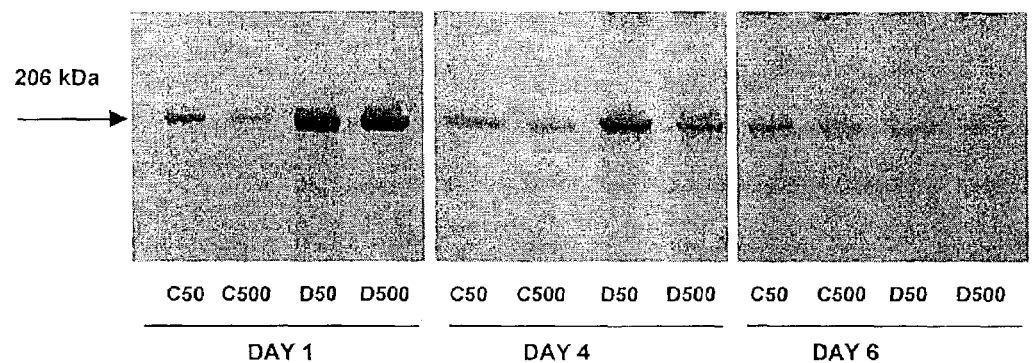
FIG. 3 shows a representative autoradiograph of newly synthesized collagen IV in renal proximal tubular cells sublethally injured by S-(1,2-dichlorovinyl)-L-cysteine in the presence of either 50 μM or 500 μM L-ascorbic acid-2-phosphate. Renal proximal tubular cells were exposed to S-(1,2-dichlorovinyl)-L-cysteine (200 μM) for 1.75 hours, and metabolically labeled with [$^{35}$S]-L-methionine for 24 hours on days 1, 4, and 6 following injury. Collagen IV immunoprecipitates were subjected to SDS-PAGE and exposed to film for 3 weeks. The molecular weight of collagen IV is 206 kilodaltons. C50, uninjured renal proximal tubular cells grown in 50 μM L-ascorbic acid-2-phosphate; C500, uninjured renal proximal tubular cells grown in 500 μM L-ascorbic acid-2-phosphate; D50, S-(1,2-dichlorovinyl)-L-cysteine-treated renal proximal tubular cells grown in 50 μM L-ascorbic acid-2-phosphate; D500, S-(1,2-dichlorovinyl)-L-cysteine-treated renal proximal tubular cells grown in 500 μM AscP.
Figure 4:
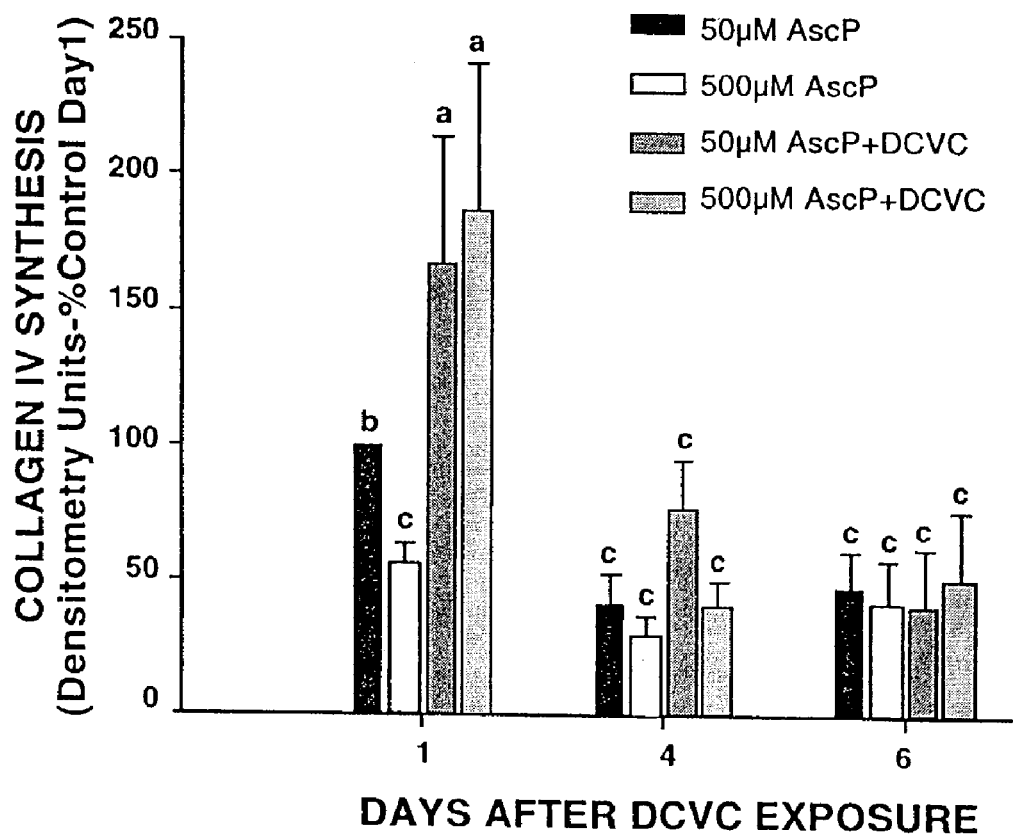
FIG. 4 shows newly synthesized collagen IV in renal proximal tubular cells sublethally injured by S-(1,2-dichlorovinyl)-L-cysteine in the presence of either 50 μM or 500 μM L-ascorbic acid-2-phosphate. Renal proximal tubular cells were exposed to S-(1,2-dichlorovinyl)-L-cysteine (200 μM) for 1.75 hours, and metabolically labeled with [$^{35}$S]-L-methionine for 24 hours on days 1, 4, and 6 following injury. Collagen IV bands visualized by autoradiography were analyzed using densitometry of scanned images. Data are presented as means±SEM, n=4 separate experiments. Bars labeled with different letter symbols are significantly different from each other (P<0.05).

FIG. 3 shows a representative autoradiograph of newly synthesized, but not deposited, [$^{35}$S]-labeled collagen IV in renal proximal tubular cells following exposure to S-(1,2-dichlorovinyl)-L-cysteine. Densitometrical analysis of the 206 kDa collagen IV band was performed on scanned images of individual autoradiographs from 4 separate experiments (FIG. 4). To illustrate changes in collagen IV synthesis over time in each group, values are expressed as a percent of day 1 controls grown in 50 μM AscP. Collagen IV synthesis on day 1 was decreased in uninjured renal proximal tubular cells grown in 500 μM AscP compared to those grown in 50 μM L-ascorbic acid-2-phosphate. One day after S-(1,2-dichlorovinyl)-L-cysteine exposure, there was an equivalent 1.8-fold increase in collagen IV synthesis in renal proximal tubular cells grown in both 50 μM and 500 μM L-ascorbic acid-2-phosphate. Levels of collagen IV synthesis at days 4 and 6 following S-(1,2-dichlorovinyl)-L-cysteine exposure and in controls were reduced compared to day 1 in renal proximal tubular cells grown in both 50 μM and 500 μM L-ascorbic acid-2-phosphate. No significant differences between groups were found on days 4 and 6. These findings demonstrate that renal proximal tubular cells sublethally injured by S-(1,2-dichlorovinyl)-L-cysteine increase collagen IV synthesis one day after the injury. However, this stimulation is independent of the concentration of ascorbic acid.

EXAMPLE 14

Deposition of Collagen IV

Figure 5:
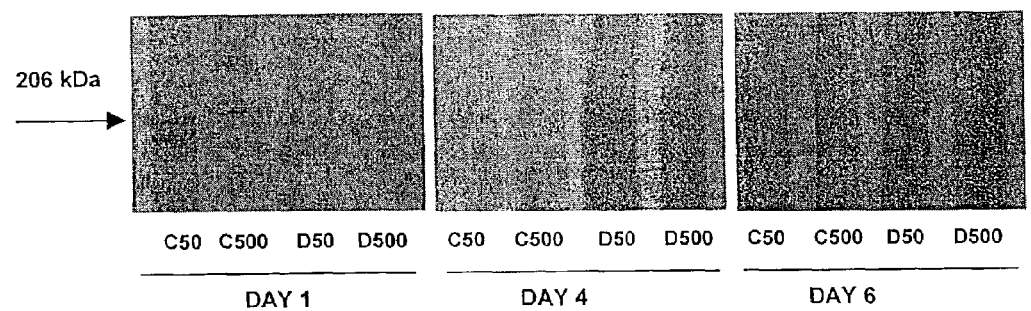
FIG. 5 shows a representative autoradiograph of newly deposited collagen IV in renal proximal tubular cells sublethally injured by S-(1,2-dichlorovinyl)-L-cysteine in the presence of either 50 μM or 500 μM L-ascorbic acid-2-phosphate. Renal proximal tubular cells were exposed to S-(1,2-dichlorovinyl)-L-cysteine (200 μM) for 1.75 hours, and metabolically labeled with [$^{35}$S]-L-methionine for 24 hours on days 1, 4, and 6 following injury. Collagen IV immunoprecipitates were subjected to SDS-PAGE and exposed to film for 3 weeks. The molecular weight of collagen IV is 206 kilodaltons. C50, uninjured renal proximal tubular cells grown in 50 µM L-ascorbic acid-2-phosphate; C500, uninjured renal proximal tubular cells grown in 500 µM L-ascorbic acid-2-phosphate; D50, S-(1,2-dichlorovinyl)-L-cysteine-treated renal proximal tubular cells grown in 50 µM L-ascorbic acid-2-phosphate; D500, S-(1,2-dichlorovinyl)-L-cysteine-treated renal proximal tubular cells grown in 500 µM L-ascorbic acid-2-phosphate.
Figure 6:
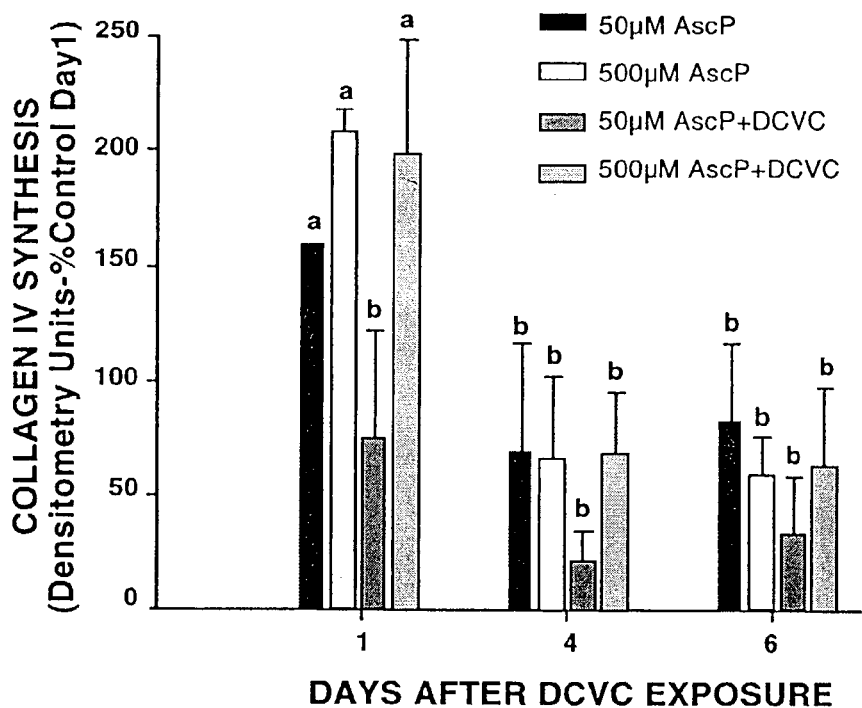
FIG. 6 shows newly deposited collagen IV in renal proximal tubular cells sublethally injured by S-(1,2-dichlorovinyl)-L-cysteine in the presence of either 50 µM or 500 µM L-ascorbic acid-2-phosphate. Renal proximal tubular cells were exposed to S-(1,2-dichlorovinyl)-L-cysteine (200 µM) for 1.75 hours, and metabolically labeled with [$^{35}$S]-L-methionine for 24 hours on days 1, 4, and 6 following injury. Collagen IV bands visualized by autoradiography were analyzed using densitometry of scanned images. Data are presented as means±SEM, n=3 separate experiments. Bars labeled with different letter symbols are significantly different from each other ($P<0.05$).

FIG. 5 shows a representative autoradiograph of newly deposited [$^{35}$S]-labeled collagen IV in renal proximal tubular cells following exposure to S-(1,2-dichlorovinyl)-L-cysteine. Densitometrical analysis of the 206 kDa collagen IV band was performed on scanned images of individual autoradiographs from 3 separate experiments (FIG. 6). To illustrate changes in collagen IV deposition over time in each group, values are expressed as a percent of day 1 controls grown in 50 μM L-ascorbic acid-2-phosphate. There was a numerical increase in collagen IV deposition by uninjured renal proximal tubular cells cultured in pharmacological concentrations of L-ascorbic acid-2-phosphate compared to renal proximal tubular cells cultured in physiological concentrations of L-ascorbic acid-2-phosphate. However, this numerical increase was not statistically significant. One day after S-(1,2-dichlorovinyl)-L-cysteine exposure, collagen IV deposition was significantly inhibited in cells grown in the presence of 50 μM L-ascorbic acid-2-phosphate. Collagen IV deposition was numerically decreased approximately 50% compared to controls in S-(1,2-dichlorovinyl)-L-cysteine-injured renal proximal tubular cells grown in physiological concentrations of L-ascorbic acid-2-phosphate on day 4 after injury, though this decrease was not statistically significant. However, S-(1,2-dichlorovinyl)-L-cysteine-injured renal proximal tubular cells grown in 500 μM L-ascorbic acid-2-phosphate maintained collagen IV deposition at levels equal to that of controls throughout the experiment. Compared to day 1, a decrease in collagen IV deposition was seen in all groups on days 4 and 6. On day 6, there were no differences in collagen IV deposition between any treatment groups. These findings demonstrate that renal proximal tubular cells sublethally injured by S-(1,2-dichlorovinyl)-L-cysteine in the presence of physiological concentrations of ascorbic acid decrease collagen IV deposition after the injury. However, in the presence of pharmacological concentrations of ascorbic acid, sublethally injured renal proximal tubular cells maintain collagen IV deposition at levels equal to controls.

EXAMPLE 15

Proline Hydroxylation in Collagen IV

Figure 7:
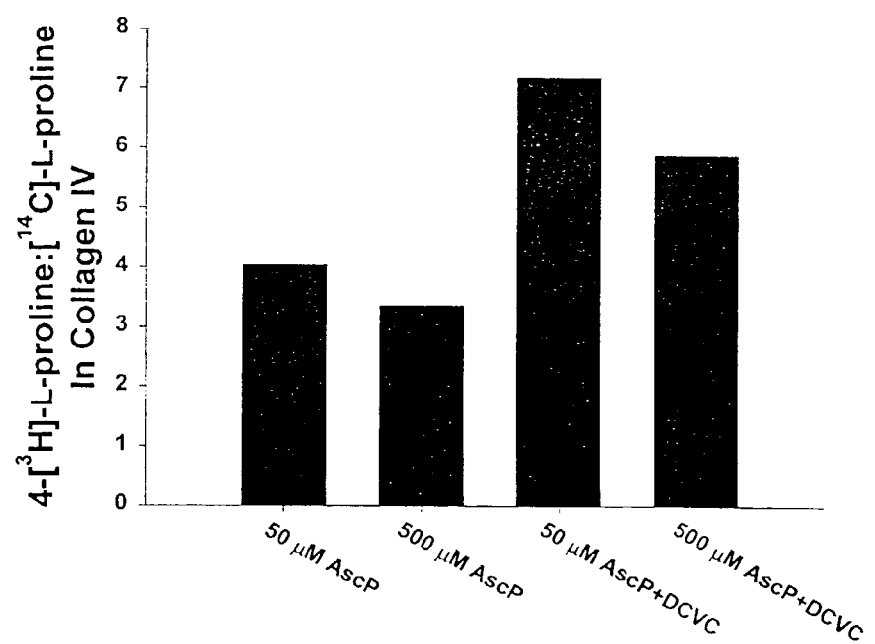
FIG. 7 shows 4-[$^3$H]-L-proline:[$^{14}$C]-L-proline content as a measure of proline hydroxylation in newly synthesized collagen IV. Renal proximal tubular cells grown in the presence of either 50 µM or 500 µM L-ascorbic acid-2-phosphate were exposed to S-(1,2-dichlorovinyl)-L-cysteine (200 µM) for 1.75 hours, and the ratio of 4-[$^3$H]-L-proline:[$^{14}$C]-L-proline in collagen IV was measured on day 1 following DCVC exposure. A higher ratio of 4-[$^3$H]-L-proline:[$^{14}$C]-L-proline represents a decrease in proline hydroxylation. Data are presented as means, n=2 separate experiments.

Loss of [$^3$H] due to hydroxylation of the 4-trans position of proline in newly synthesized collagen IV was used as a marker of prolyl hydroxylase activity. Renal proximal tubular cells grown in 50 μM and 500 μM AscP were dual labeled with 4-[$^3$H]-L-proline and [$^{14}$C]-L-proline over a 24 hour period following S-(1,2-dichlorovinyl)L-cysteine exposure, and the loss of [$^3$H] was measured as a decrease in the ratio of 4-[$^3$H]-L-proline:[$^{14}$C]-L-proline. S-(1,2-dichlorovinyl)-L-cysteine-injured renal proximal tubular cells grown in 50 μM AscP had a ratio of 4-[$^3$H]-L-proline:[$^{14}$C]-L-proline that was approximately 80% greater than controls on day 1 following injury indicating a significant decrease in proline hydroxylation (FIG. 7). 4-[$^3$H]-L-proline: [$^{14}$C]-L-proline ratio in S-(1,2-dichlorovinyl)-L-cysteine-injured renal proximal tubular cells grown in 500 μM AscP was approximately 45% greater than controls on day 1 following injury. These data suggest that S-(1,2-dichlorovinyl)-L-cysteine exposure inhibits prolyl hydroxylase activity, and that decreased proline hydroxylation may contribute to the inhibition of collagen IV deposition in S-(1,2-dichlorovinyl)-L-cysteine-injured renal proximal tubular cells grown in 50 μM L-ascorbic acid-2-phosphate. In contrast, the degree of proline hydroxylation in newly synthesized collagen IV is higher in S-(1,2-dichlorovinyl)-L-cysteine-injured renal proximal tubular cells grown in the presence of 500 μM L-ascorbic acid-2-phosphate, suggesting that ascorbic acid-stimulated prolyl hydroxylase activity may contribute in part to the deposition of collagen IV in S-(1,2-dichlorovinyl)-L-cysteine-injured RPTC.

EXAMPLE 16

Effect of Exogenous Extracellular Matrix Proteins on Cell Repair

Because S-(1,2-dichlorovinyl)-L-cysteine-injured renal proximal tubular cells cultured in the presence of pharmacological concentrations of L-ascorbic acid-2-phosphate maintain collagen IV deposition and are capable of physiological repair, whether exogenous renal tubular extracellular matrix proteins promoted cell repair in S-(1,2-dichlorovinyl)-L-cysteine-injured renal proximal tubular cells was determined. DCVC-injured renal proximal tubular cells grown in physiological concentrations of L-ascorbic acid-2-phosphate were exposed to exogenous collagen I or collagen IV (0, 5, 15, 50 μg/ml) immediately following S-(1, 2-dichlorovinyl)-L-cysteine exposure and continuously through day 6 after injury. Basal $QO_2$ and monolayer cell density were measured on days 1 and 6 after injury induced by DCVC.

Figure 8A:
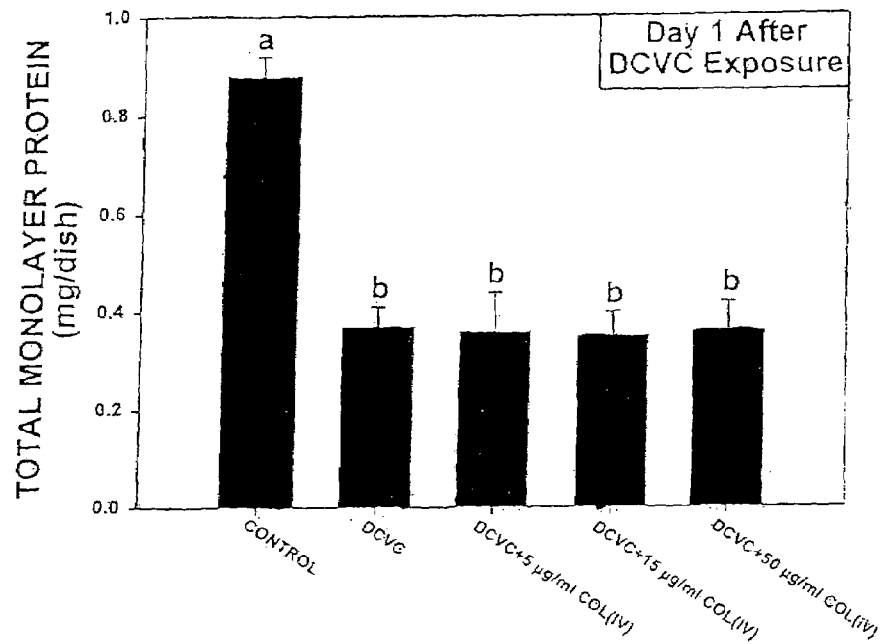
FIGS. 8A–8B show total protein content in renal proximal tubular cells sublethally injured by S-(1,2-dichlorovinyl)-L-cysteine and cultured in the presence of collagen IV. Renal proximal tubular cells were exposed to S-(1,2-dichlorovinyl)-L-cysteine (200 µM) for 1.75 hours, and collagen IV was added immediately following S-(1,2-dichlorovinyl)-L-cysteine exposure and after daily media change at the indicated concentrations. Protein content was measured on days 1 (FIG. 8A) and 6 (FIG. 8B) following injury. Data are presented as means ±SEM, n=4–5 separate experiments. Bars labeled with different letter symbols are significantly different from each other ($P<0.05$).
Figure 8B:
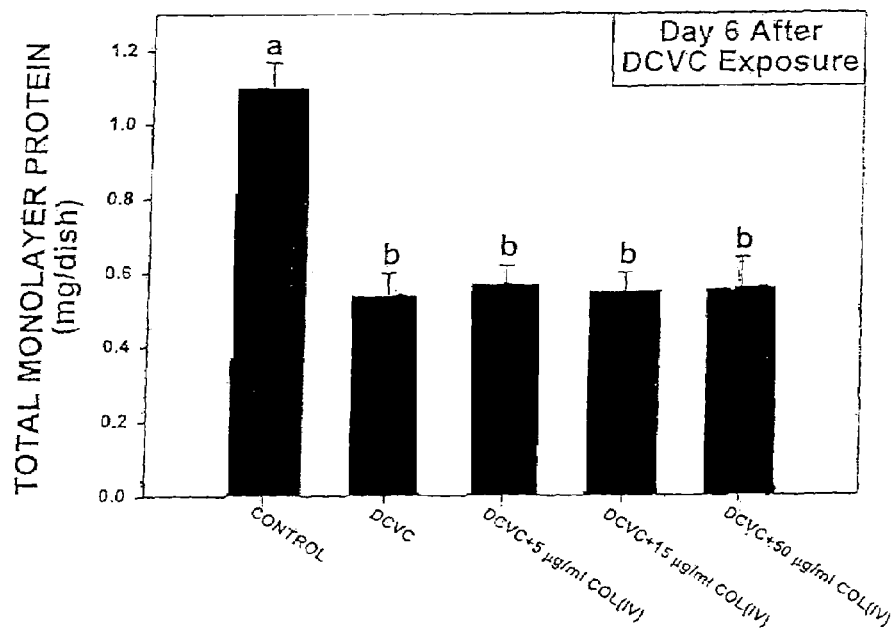
Figure 9A:
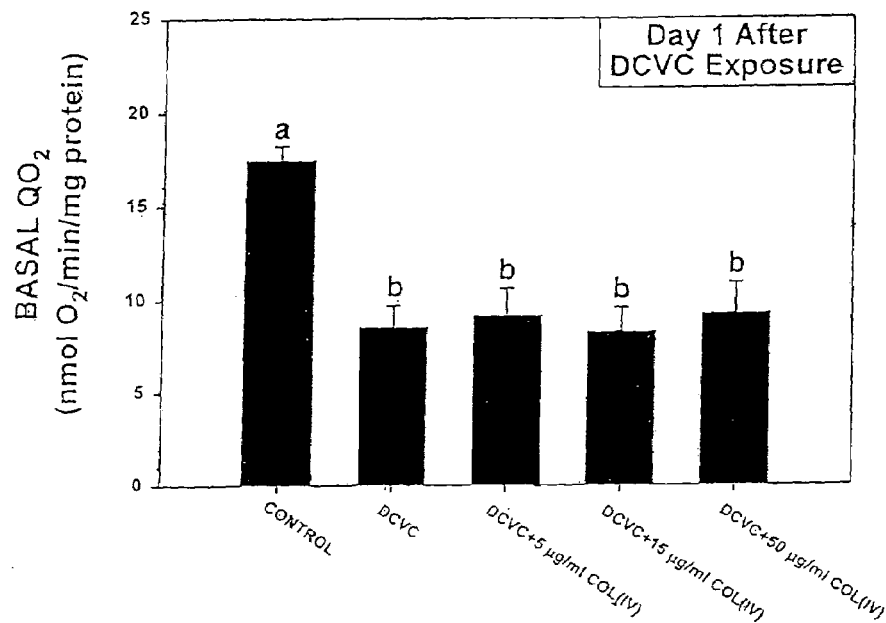
FIGS. 9A–9B show basal oxygen consumption in renal proximal tubular cells sublethally injured by S-(1,2-dichlorovinyl)-L-cysteine and cultured in the presence of collagen IV. Renal proximal tubular cells were exposed to S-(1,2-dichlorovinyl)-L-cysteine (200 µM) for 1.75 hours, and collagen IV was added immediately following S-(1,2-dichlorovinyl)-L-cysteine exposure and after daily media change at the indicated concentrations. $QO_2$ was measured on days 1 (FIG. 9A) and 6 (FIG. 9B) following injury. Data are presented as means ±SEM, n=4–5 separate experiments. Bars labeled with different letter symbols are significantly different from each other ($P<0.05$).
Figure 9B:
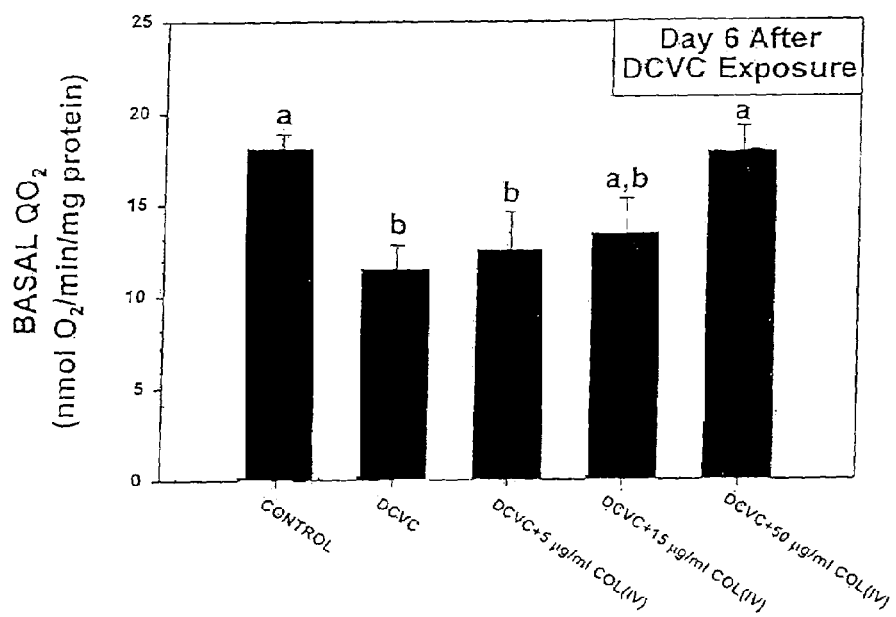
Figure 10A:
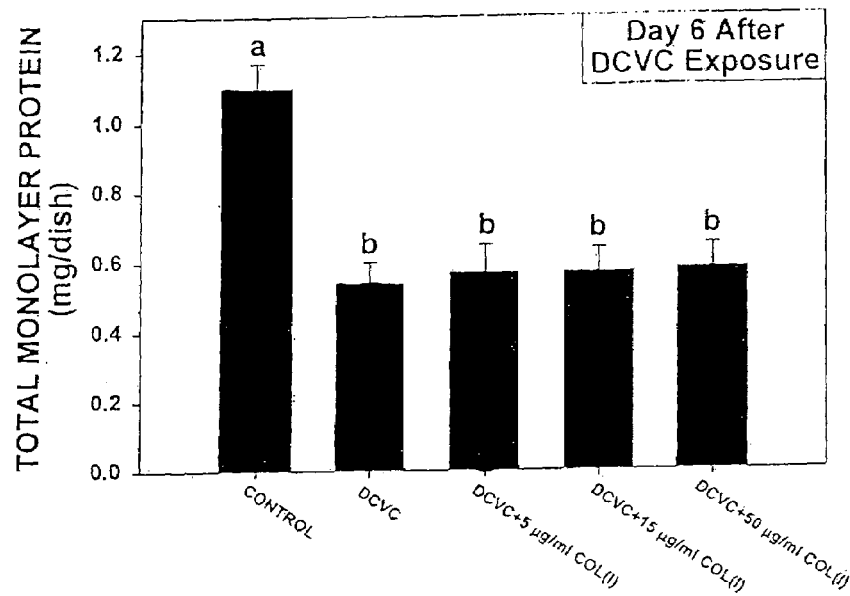
FIGS. 10A–10B show total protein content and basal oxygen consumption in renal proximal tubular cells sublethally injured by S-(1,2-dichlorovinyl)-L-cysteine and cultured in the presence of collagen I. Renal proximal tubular cells were exposed to S-(1,2-dichlorovinyl)-L-cysteine (200 µM) for 1.75 hours, and collagen I was added immediately following S-(1,2-dichlorovinyl)-L-cysteine exposure and after daily media change at the indicated concentrations. Total protein and $QO_2$ measured on day 6 after injury are shown in the FIG. 10A and FIG. 10B, respectively. Data are presented as means ±SEM, n=4–5 separate experiments. Bars labeled with different letter symbols are significantly different from each other ($P<0.05$).
Figure 10B:
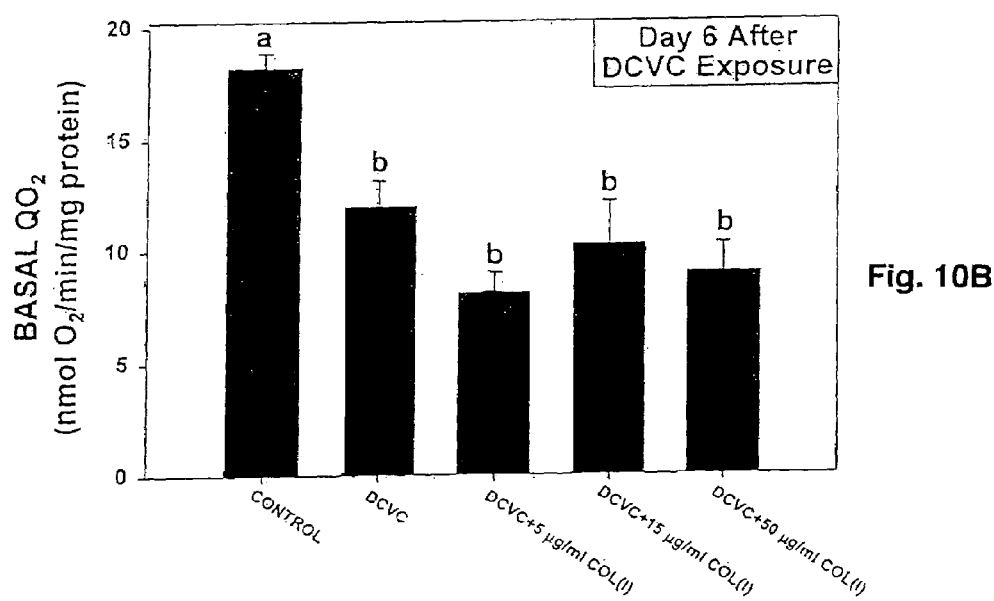

Exposure of untreated renal proximal tubular cells to collagen I or collagen IV had no effect on basal $QO_2$ or monolayer cell density on days 1 or 6. On day 1 after injury, monolayer cell density and basal $QO_2$ were decreased approximately 50% in injured renal proximal tubular cells grown in the absence or presence of collagen IV (FIGS. 8A and 9A) and collagen I. On day 6, cell density in injured renal proximal tubular cells cultured in the presence of collagen IV remained approximately 50% of that of uninjured renal proximal tubular cells and equal to the cell density in S-(1,2-dichlorovinyl)-L-cysteine-injured renal proximal tubular cells grown in the absence of collagen IV (FIG. 8B). However, S-(1,2-dichlorovinyl)-L-cysteine-injured renal proximal tubular cells cultured in the presence of exogenous collagen IV recovered basal $QO_2$ by day 6 after injury, with complete repair in renal proximal tubular cells grown in the presence of 50 μg/ml collagen IV (FIG. 9B). DCVC-injured renal proximal tubular cells cultured in the presence of collagen I exhibited neither increased cell density nor repair of basal $QO_2$ by day 6 after injury (FIG. 10).

Figure 11A:
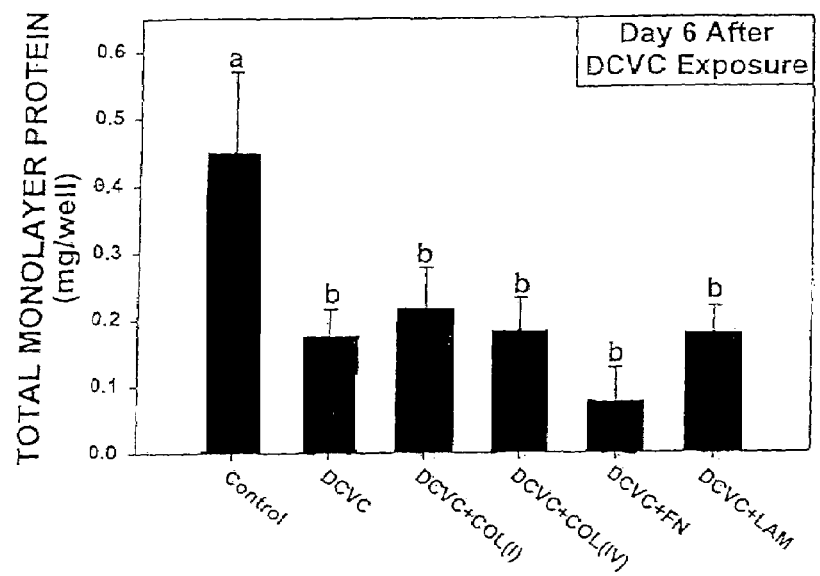
FIGS. 11A–11B show total protein content and $Na^+/K^+$-ATPase activity in renal proximal tubular cells sublethally injured by S-(1,2-dichlorovinyl)-L-cysteine and cultured in the presence of exogenous extracellular matrix proteins. Renal proximal tubular cells were exposed to S-(1,2-dichlorovinyl)-L-cysteine (200 µM) for 1.75 hours, and collagen I, collagen IV, laminin, or fibronectin was added immediately following S-(1,2-dichlorovinyl)-L-cysteine exposure and after daily media change at a concentration of 50 µg/ml. Total protein and $Na^+/K^+$-ATPase activity measured on day 6 after injury are shown in the FIG. 11A and FIG. 11B, respectively. Data are presented as means±SEM, n=3–4 separate experiments. Bars labeled with different letter symbols are significantly different from each other ($P<0.05$).
Figure 11B:
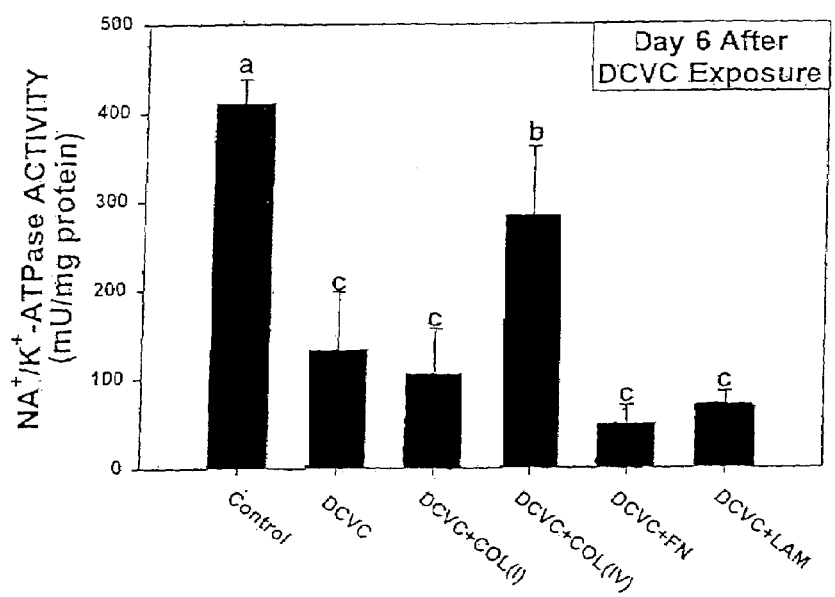

The effects of fibronectin and laminin on cell density, and the effects of collagen I, collagen IV, laminin, and fibronectin on the repair of $Na^+/K^+$-ATPase activity in sublethally injured renal proximal tubular cells was determined next. S-(1,2-dichlorovinyl)-L-cysteine -injured renal proximal tubular cells grown in physiological concentrations of AscP were exposed to exogenous collagen I, collagen IV, laminin in, or fibronectin immediately following S-(1,2-dichlorovinyl)-L-cysteine exposure and through day 6 after injury. Exogenous proteins were added directly to culture media at a concentration of 50 μg/ml, because this concentration of collagen IV was found to promote complete repair (FIG. 9B). The addition of exogenous collagen I, collagen IV, fibronectin, or laminin to injured renal proximal tubular cells produced no change in monolayer protein content on day 1 or day 6 (FIG. 11A). These results suggest that, like collagen I and collagen IV, exogenous laminin or fibronectin does not stimulate injured renal proximal tubular cells to proliferate. $Na^+/K^+$-ATPase activity was significantly increased in injured renal proximal tubular cells cultured in the presence of collagen IV on day 6 following S-(1,2-dichlorovinyl)-L-cysteine injury (FIG. 11B). $Na^+/K^+$-ATPase activity remained inhibited on day 6 after injury in renal proximal tubular cells cultured in the presence of exogenous collagen I, fibronectin, or laminin (FIG. 11B). These results, and those illustrated in FIG. 9B, suggest that repair of physiological functions in S-(1,2-dichlorovinyl)-L-cysteine-injured renal proximal tubular cells is a process mediated specifically by extracellular collagen IV.

Discussion

Renal proximal tubular cells that do not die or become detached from the extracellular matrix following ischemic or chemical injury are thought to undergo repair or to dedifferentiate, proliferate, and migrate to denuded areas of the tubules. The cells of the newly lined tubule may then differentiate, promoting the return of normal tubular function and overall renal function. During studies of the mechanisms of renal proximal tubular cell repair and regeneration following toxicant exposure, renal proximal tubular cells sublethally injured by S-(1,2-dichlorovinyl)-L-cysteine neither proliferated nor repaired physiological functions (38). In contrast, renal proximal tubular cells sublethally injured by the oxidant t-butyl hydroperoxide proliferated and repaired physiological functions (37). However, when renal proximal tubular cells sublethally injured by S-(1,2-dichlorovinyl)-L-cysteine were cultured in the presence of pharmacological concentrations of L-ascorbic acid-2-phosphate, they proliferated and repaired physiological functions (39). Thus, the mechanism of action of pharmacological concentrations of ascorbic acid in promoting renal proximal tubular cell repair and regeneration may be through the stimulation of the synthesis and deposition of collagen IV.

AscP is known to promote collagen synthesis and deposition in cultured cells (13, 33). Collagen IV is the most abundant component of the proximal tubular basement membrane, and the regulation of collagen IV synthesis and degradation plays an important role in cell function, growth, migration, and organ remodeling in many tissues (15). Further, collagen IV synthesis and deposition is increased in control renal proximal tubular cells exposed to L-ascorbic acid-2-phosphate (39). Collagen IV synthesis and deposition in renal proximal tubular cells sublethally injured by S-(1,2-dichlorovinyl)-L-cysteine was examined. One day after S-(1,2-dichlorovinyl)-L-cysteine exposure, collagen IV synthesis increased in renal proximal tubular cells grown in the presence of physiological concentrations of L-ascorbic acid-2-phosphate and decreased to control levels on days 4 and 6. In contrast, collagen IV deposition into the extracellular matrix was inhibited by S-(1,2-dichlorovinyl)-L-cysteine one day after exposure, a trend that was still evident on day 4, although the statistical significance of this decrease was not conclusive due to a significant decrease in collagen IV deposition in all treatment groups. These observations represent the novel findings 1) that an increase in collagen IV synthesis is a response to S-(1,2-dichlorovinyl)-L-cysteine injury and 2) that one potential toxic mechanism of S-(1,2-dichlorovinyl)-L-cysteine-induced nephrotoxicity is the inhibition of collagen IV deposition into the ECM. These observations suggest that the lack of repair and regeneration in S-(1,2-dichlorovinyl)-L-cysteine-injured renal proximal tubular cells grown in physiological concentrations of ascorbic acid may result from an inability to deposit collagen IV in response to injury.

Examination of collagen IV synthesis and deposition in renal proximal tubular cells grown in pharmacological concentrations of L-ascorbic acid-2-phosphate showed that injury by S-(1,2-dichlorovinyl)-L-cysteine increased collagen IV synthesis, as shown by S-(1,2-dichlorovinyl)-L-cysteine-injured renal proximal tubular cells grown in physiological concentrations of ascorbic acid. Unlike S-(1,2-dichlorovinyl)-L-cysteine-injured renal proximal tubular cells grown in physiological concentrations of L-ascorbic acid-2-phosphate, S-(1,2-dichlorovinyl)-L-cysteine-injured renal proximal tubular cells grown in pharmacological concentrations of L-ascorbic acid-2-phosphate maintained collagen IV deposition at control levels. These data suggest that the maintenance of collagen IV deposition after S-(1,2-dichlorovinyl)-L-cysteine exposure promotes renal proximal tubular cell repair and regeneration by day 6 after injury, thus creating an association between the ability of injured renal proximal tubular cells to deposit collagen IV and to repair physiological functions.

One potential explanation for the lack of collagen IV deposition in S-(1,2-dichlorovinyl)-L-cysteine-injured renal proximal tubular cells grown in physiological concentrations of L-ascorbic acid-2-phosphate is that newly synthesized procollagen α chains are not being properly hydroxylated at susceptible proline residues. Underhydroxylated procollagen α chains will not fold into triple helical monomers adequately, and most are targeted for degradation intracellularly rather than being secreted into the extracellular matrix (18, 47). Prolyl hydroxylase is the microsomal enzyme responsible for proline hydroxylation of procollagen α chains, and ascorbic acid is the preferred iron reducing cofactor for prolyl hydroxylase activity (41). Approximately 45%–50% of susceptible collagen proline residues are hydroxylated in normal vertebrate tissues; however, when the degree of proline hydroxylation is decreased, so is the amount of collagen deposited into the extracellular matrix (28). In this study, proline hydroxylation in newly synthesized collagen IV was decreased following S-(1,2-dichlorovinyl)-L-cysteine exposure in renal proximal tubular cells grown in the presence of physiological concentrations of AscP. However, proline hydroxylation in injured renal proximal tubular cells grown in pharmacological concentrations of L-ascorbic acid-2-phosphate was greater compared to injured renal proximal tubular cells grown in physiological concentrations of L-ascorbic acid-2-phosphate, suggesting that these cells retain some ability to hydroxylate susceptible proline residues. Although there is no evidence of a direct interaction between S-(1,2-dichlorovinyl)-L-cysteine and prolyl hydroxylase, these results suggest that insufficient proline hydroxylation contributes to decreased collagen IV deposition in S-(1,2-dichlorovinyl)-L-cysteine-injured renal proximal tubular cells grown in physiological concentrations of L-ascorbic acid-2-phosphate. In addition, pharmacological concentrations of L-ascorbic acid-2-phosphate increase the degree of proline hydroxylation in collagen IV after S-(1,2-dichlorovinyl)-L-cysteine injury and may promote the maintenance of collagen IV deposition into the ECM. These results further support the conclusion that the deposition of collagen IV is associated with renal proximal tubular cell repair following sublethal injury.

FIG. 4 shows that uninjured renal proximal tubular cells grown in pharmacological concentrations of L-ascorbic acid-2-phosphate synthesize less collagen IV on day 1 after confluence than renal proximal tubular cells grown in physiological concentrations of L-ascorbic acid-2-phosphate. This finding can be explained by the idea that renal proximal tubular cell cultures synthesize less collagen over time, especially after reaching confluence, as the cultures begin to quiesce. This hypothesis is supported by previous studies in regenerating tissues demonstrating upregulated extracellular matrix protein expression that returns to basal levels when tissue structure is restored (49). Because ascorbate is known to enhance cellular growth, renal proximal tubular cells grown in pharmacological L-ascorbic acid-2-phosphate concentrations may decrease collagen synthesis to basal levels sooner than renal proximal tubular cells grown in physiological concentrations of L-ascorbic acid-2-phosphate (36). Further evidence of this effect is observed on day 4, when renal proximal tubular cells cultured in physiological L-ascorbic acid-2-phosphate concentrations exhibit collagen IV synthesis that is decreased to levels of renal proximal tubular cells cultured in pharmacological concentrations of L-ascorbic acid-2-phosphate.

Next, the effect of exogenous collagens I and IV, laminin, and fibronectin on cell repair was determined in renal proximal tubular cells sublethally injured by S-(1,2-dichlorovinyl)-L-cysteine. Based on the correlation between cell repair and collagen IV deposition, it was hypothesized that adding exogenous collagen IV to the culture media would promote cell repair and/or proliferation in S-(1,2-dichlorovinyl)-L-cysteine-injured renal proximal tubular cells. In addition, by determining the effects of collagen I, laminin, or fibronectin on cell repair, whether collagen IV-stimulated repair is specific to collagen IV or due to a general effect of extracellular matrix proteins was determined. Collagen IV, but not collagen I, laminin, or fibronectin, promoted repair of mitochondrial oxygen consumption (basal $QO_2$) and active $Na^+$ transport ($Na^+/K^+$-ATPase activity) following injury, implicating collagen IV as an important extracellular matrix protein involved in repair of physiological functions in RPTC. However, S-(1,2-dichlorovinyl)-L-cysteine-injured renal proximal tubular cells cultured in the presence of collagen IV did not exhibit increased cell density on day 6 following S-(1,2-dichlorovinyl)-L-cysteine exposure. This finding suggests that collagen IV is not involved in the proliferation of renal proximal tubular cells, as observed in the presence of pharmacological concentrations of L-ascorbic acid-2-phosphate, and that ascorbic acid plays other important roles in renal recovery not related to extracellular matrix production. These data provide strong evidence of a specific role for collagen IV in cell repair, but not proliferation, following sublethal injury.

The non-pathological role of collagen IV in renal injury, repair, and restoration of tubular function is relatively unknown. The novel findings presented here suggest that extracellular collagen IV specifically promotes the repair of physiological functions in injured RPTC. The extracellular matrix proteins collagen I, laminin, and fibronectin did not promote repair of physiological functions. S-(1,2-dichlorovinyl)-L-cysteine-injured renal proximal tubular cells exhibited decreased collagen IV hydroxylation and deposition and were unable to repair physiological functions. In contrast, renal proximal tubular cells grown in pharmacological concentrations of L-ascorbic acid-2-phosphate maintained collagen IV hydroxylation and deposition and were able to repair physiological functions and increase cell density after DCVC injury. Therefore, there is a correlation between AscP-stimulated hydroxylation and deposition of collagen IV and the ability of injured renal proximal tubular cells to repair physiological functions.

EXAMPLE 17

Materials

Female New Zealand White rabbits (1.5–2.0 kg) were purchased from Myrtle's Rabbitry (Thompson Station, Tenn.). S-(1,2-dichlorovinyl)-L-cysteine was a gift from Dr. T. W. Petry (Pharmacia Upjohn, Kalamazoo, Mich.) and was synthesized as previously described (Moore and Green, 1988). L-Ascorbic acid-2-phosphate (magnesium salt) was purchased from Wako Chemicals USA, Inc. (Richmond, Va.). Ouabain was obtained from RBI/Sigma (Natick, Mass.). FITC-conjugated goat anti-mouse IgG and mouse monoclonal antibodies directed against human integrin subunits $\alpha_1$ (clone FB12), $\alpha_2$ (clone JBS2), and $\beta_1$ (clone B3B11) were purchased from Chemicon International, Inc. (Temecula, Calif.). All other materials were purchased from Sigma Chemical Co. (St. Louis, Mo.).

EXAMPLE 18

Isolation of Proximal Tubules and Culture Conditions

Rabbit renal proximal tubules were isolated using the iron oxide perfusion method and grown in 35-mm tissue culture dishes or 48-well cell culture clusters under improved conditions as previously described (Nowak and Schnellmann, 1995; Nowak and Schnellmann, 1996). The cell culture medium was a 1:1 mixture of DMEM/Ham's F-12 (without D-glucose, phenol red, or sodium pyruvate) supplemented with 15 mM HEPES buffer, 2.5 mM L-glutamine, 1 μM pyridoxine HCl, 15 mM sodium bicarbonate, and 6 mM lactate. Hydrocortisone (50 nM), selenium (5 ng/ml), human transferrin (5 μg/ml), bovine insulin (10 nM), and L-ascorbic acid-2-phosphate (50 or 500 μM) were added to the culture medium immediately prior to daily media change. L-Ascorbic acid-2-phosphate (AscP) was used because L-ascorbic acid is unstable in culture media. AscP is stable in culture media and, after intracellular dephosphorylation, has the same effect on cultured cells as L ascorbic acid (Hata and Senoo, 1989).

EXAMPLE 19

Sublethal Injury of RPTC

Confluent monolayers of renal proximal tubular cells (day 6 after seeding) were exposed to 200 μM S-(1,2-dichlorovinyl)-L-cysteine (dissolved in water) for 1.75 hours followed by toxicant removal and addition of fresh culture media. This method produces approximately 50% cell death and loss 24 hours after the exposure. In some experiments, exogenous collagen IV (50 μg/ml), collagen I (50 μg/ml), or function-stimulating antibodies to collagen-binding integrin subunits $\alpha_2$ or $\beta_1$ (5 μg/ml) was added daily to the culture media of S-(1,2-dichlorovinyl)-L-cysteine-injured renal proximal tubular cells cultured in the absence of pharmacological concentrations of L-ascorbic acid-2-phosphate. Function-stimulating antibodies to collagen-binding integrin $\alpha_1$ are not commercially available at this time. On days 1 and 6 following S-(1,2-dichlorovinyl)-L-cysteine exposure, active $Na^+$ transport or $Na^+/K^+$-ATPase activity, and collagen-binding integrin expression and/or localization in the remaining sublethally injured renal proximal tubular cells was determined as described below.

EXAMPLE 20

Active $Na^+$ Transport

Renal proximal tubular cells were gently detached from culture dishes with a rubber policeman and transferred to a 37° C. oxygen consumption ($QO_2$) chamber. $QO_2$ in renal proximal tubular cells was measured polarographically in the absence (basal $QO_2$) or presence of ouabain (100 μM) (ouabain-insensitive $QO_2$) using a Clark-type electrode as described previously (Nowak and Schnellmann, 1995). Active $Na^+$ transport (ouabain-sensitive $QO_2$) was calculated by subtracting ouabain-insensitive $QO_2$ from basal $QO_2$. Protein concentrations were determined using the bicinchoninic acid microassay according to the manufacturer's instructions (Pierce, Rockford, Ill.).

EXAMPLE 21

$Na^+/K^+$-ATPase Activity

Total ATPase activity was measured as described above. Briefly, renal proximal tubular cells cultured in 48-well cell culture clusters were scraped, solubilized in dissociation buffer (5 mM HEPES (pH 7.4), 25 mM imidazole, 1% BSA, 0.065% sodium dodecyl sulfate (SDS)) for 10 min. at room temperature, and combined with fresh ATPase assay buffer (2.54 mM $MgCl_2$, 100 mM NaCl, 10 mM KCl, 5 mM HEPES, 10 U/ml lactate dehydrogenase, 7 U/ml pyruvate kinase, 2.54 mM $Na_2ATP$, 2.54 mM phospho(enol)pyruvate, and 0.5 mM β-NADH). ATPase activity was measured under linear conditions spectrophotometrically (340 nm) as the oxidation of β-NADH to $NAD^+$ at 37° C. in the absence or presence of ouabain (0.1 mM). $Na^+/K^+$-ATPase activity was calculated as total ATPase activity minus ouabain-insensitive ATPase activity.

EXAMPLE 22

Expression of Collagen-Binding integrins

CBI expression was measured by flow cytometry of renal proximal tubular cells immunostained with monoclonal antibodies to integrin subunits $\alpha_1$, $\alpha_2$, and $\beta_1$. Renal proximal tubular cell monolayers were washed 3 times with ice-cold PBS, gently scraped from culture dishes into cell culture media containing 5% BSA (BSA/media), and transferred to microcentrifuge tubes. Renal proximal tubular cells were dissociated by pipeting, incubated on ice with moderate shaking for 20 minutes, centrifuged, and resuspended in 1% BSA/media containing 2 μg/ml of a specific anti-integrin antibody or non-specific IgG on ice with moderate shaking for 1 hour. After 3 washes with 1% BSA/media, renal proximal tubular cells were incubated for 30 minutes in the dark with a goat-anti mouse FITC-conjugated IgG diluted 1:100 in 1% BSA/media, followed by 3 washes with ice-cold PBS. Membrane expression of collagen-binding integrins was determined immediately by flow cytometry using a FACSCalibur four-color cell sorter/analyzer (Beckton Dickinson, San Jose, Calif.) with a blue argon laser for detection of FITC. Specific binding was calculated as total fluorescence minus that in IgG controls.

EXAMPLE 23

Subcellular Localization of CBIs

Collagen-binding integrin localization was determined using confocal microscopy of renal proximal tubular cell monolayers stained with monoclonal antibodies to integrin subunits $\alpha_1$, $\alpha_2$, and $\beta_1$. Renal proximal tubular cell monolayers were washed 3 times with PBS and fixed with 10% buffered formalin (4% formaldehyde) for 20 minutes at room temperature. After 3 washes with PBS, monolayers were permeabilized in PTB buffer (PBS+0.3% Triton X-100+0.1% BSA) for 10 minutes at room temperature. Monolayers were washed 3 times with 0.1% BSA in PBS and incubated with 8% BSA in PBS for 30 minutes at room temperature. BSA (1%) in PBS containing 5 μg/ml of specific integrin antibodies or non-specific IgG was added to renal proximal tubular cell monolayers and incubated overnight a t 4° C. with moderate shaking. Following 3 washes with PTB buffer, monolayers were incubated for 2 hours in the dark at room temperature with 1% BSA in PBS containing a 1:100 dilution of a FITC-conjugated goat anti-mouse IgG. Monolayers were washed 3 times with PTB, and glass coverslips were applied after the addition of 2–3 drops of mounting media. Confocal microscopy was performed using a Zeiss confocal laser scanning microscope (Model 410, Carl Zeiss, Inc., Thornwood, N.Y.). Basal and apical membrane locations were determined visually in the Z-plane using light field microscopy. Two to three photomicrographs per monolayer at the basal and apical membranes were then scanned with an omnichrome laser filtered at 488 nm to detect FITC.

EXAMPLE 24

Statistical Analysis

Renal proximal tubular cells isolated from one rabbit represent one experiment (n=1) that consisted of data collected from 1–2 plates of cells. Experiments were repeated until an n of 3–6 was reached. Data are presented as means±SEM. Significant differences between treatment groups (p<0.05) were determined using SigmaStat one-way ANOVA and Student-Newman-Keuls post hoc test for the comparison of multiple means (Jandel Scientific, San Rafael, Calif.).

EXAMPLE 25

Figure 12A:
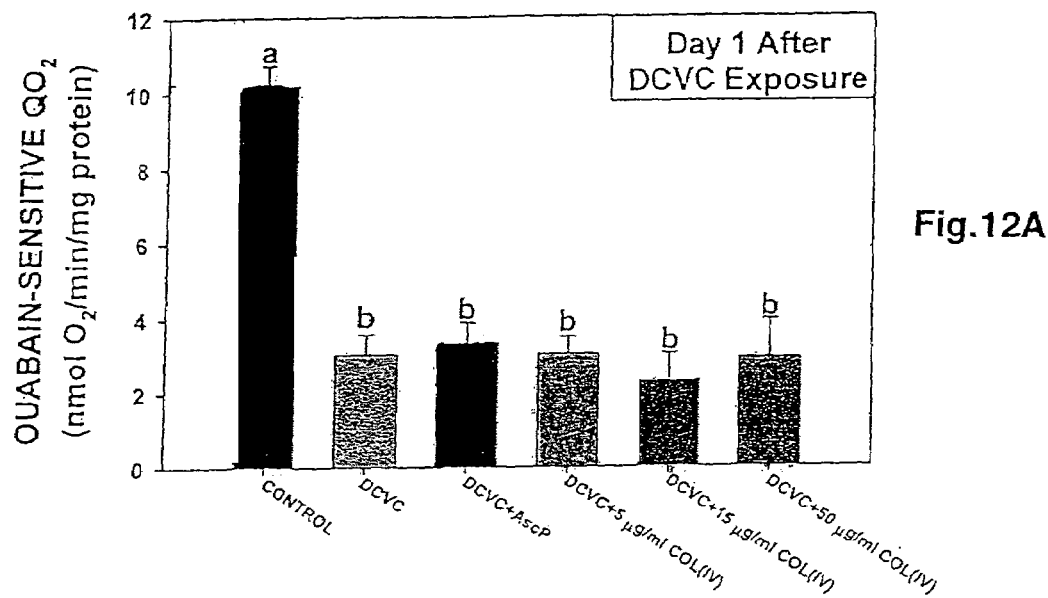
FIGS. 12A–12B show active $Na^+$ transport measured as ouabain-sensitive Q02 in renal proximal tubular cells sublethally injured by S-(1,2-dichlorovinyl)-L-cysteine and cultured in the absence or presence of exogenous collagen IV (0, 5, 15, 50 µg/ml). Ouabain-sensitive $QO_2$ was measured on days 1 (FIG. 12A) and 6 (FIG. 12B) following S-(1,2-dichlorovinyl)-L-cysteine injury. Data are presented as means ±SEM, n=4–5 separate experiments. Bars labeled with different letter symbols are significantly different from each other ($P<0.05$).
Figure 12B:
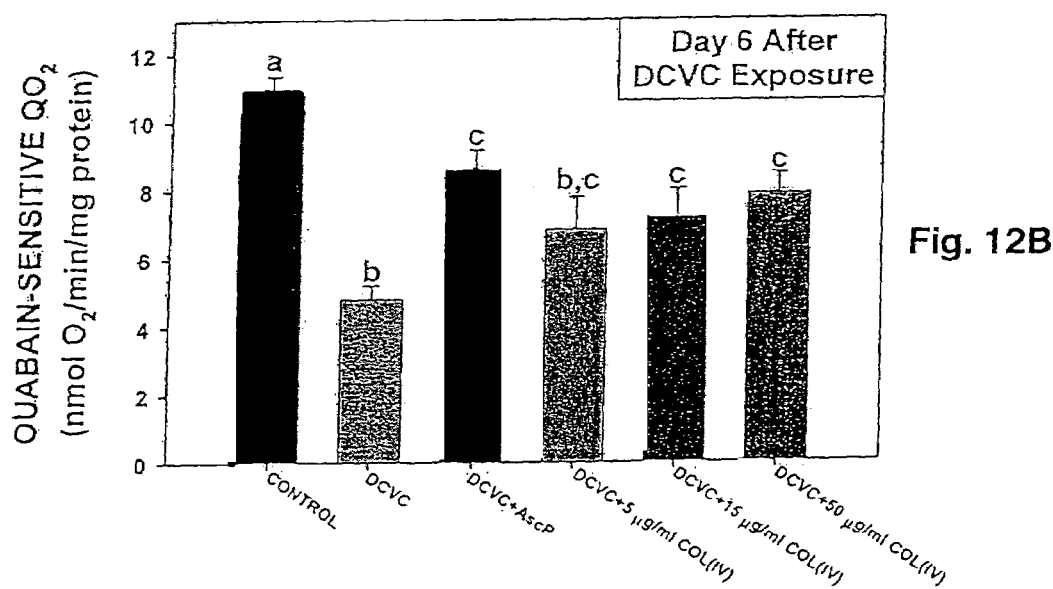

Effect of AscP and Exogenous Collagen IV on Active $Na^+$ Transport in DCVC-Injured RPTC Exposure of uninjured renal proximal tubular cells to pharmacological concentrations of L-ascorbic acid-2-phosphate or exogenous collagen IV had no effect on active $Na_+$ transport on days 1 or 6. On day 1 after injury, active $Na^+$ transport was decreased approximately 80% in injured renal proximal tubular cells grown in the absence or presence of pharmacological concentrations of L-ascorbic acid-2-phosphate or collagen IV (FIG. 12A). On day 6, S-(1,2-dichlorovinyl)-L-cysteine-injured renal proximal tubular cells cultured in the presence of exogenous collagen IV exhibited a concentration-dependent improvement in active $Na^+$ transport, similar to that seen in injured renal proximal tubular cells cultured in the presence of pharmacological concentrations of L-ascorbic acid-2-phosphate (FIG. 12B).

EXAMPLE 26

Figure 13:
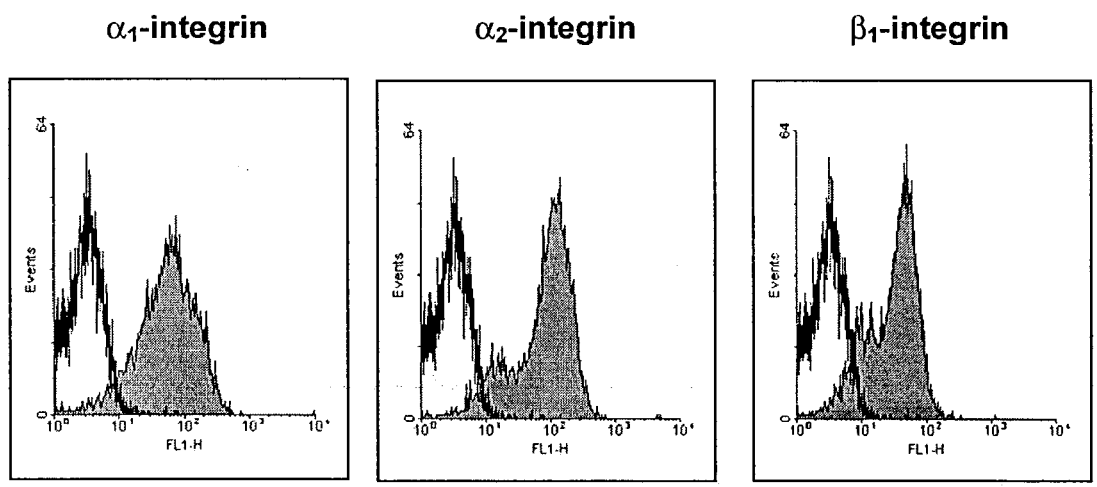
FIG. 13 shows binding of monoclonal antibodies to CBI subunits. Untreated rabbit renal proximal tubular cells were gently scraped from culture dishes and incubated with non-specific IgG or primary monoclonal antibodies to CBI subunits $\alpha_1$, $\alpha_2$, or $\beta_1$. Fluorescence intensity of FITC-conjugated goat anti-mouse secondary antibodies was measured by flow cytometry. FL1-H (x-axis) displays fluorescence intensity on a logarithmic scale. Shaded histograms represent fluorescence intensity of renal proximal tubular cells labeled with primary antibodies to CBI subunits. Open histograms represent renal proximal tubular cells incubated with a non-specific IgG.
Figure 14A:
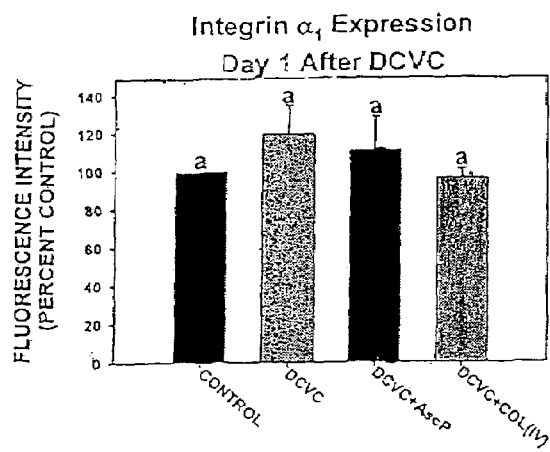
FIGS. 14A–14F show the expression of collagen-binding integrin subunits $\alpha_1$, $\alpha_2$, and $\beta_1$ in renal proximal tubular cells sublethally injured by S-(1,2-dichlorovinyl)-L-cysteine and cultured in the absence or presence of pharmacological concentrations of L-ascorbic acid-2-phosphate (500 µM) or exogenous collagen IV (50 µg/ml). On days 1 (FIGS. 14A, 14C and 14E) and 6 (FIGS. 14B, 14D and 14F) following S-(1,2-dichlorovinyl)-L-cysteine injury, plasma membrane expression of collagen-binding integrins was analyzed by flow cytometry. Fluorescence intensity is expressed as a percent of control ±SEM after subtraction of fluorescence attributed to non-specific IgG binding (n=4–6). Bars labeled with different letter symbols are significantly different from each other ($P<0.05$).
Figure 14B:
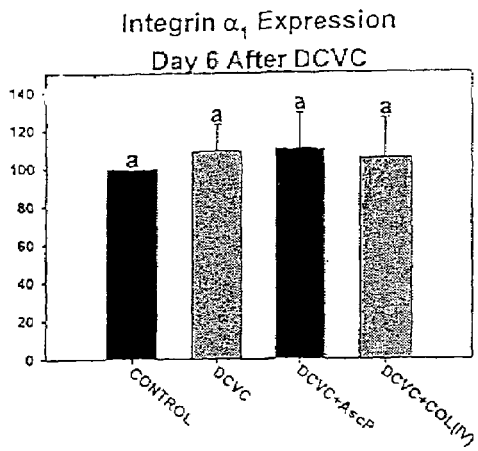
Figure 14C:
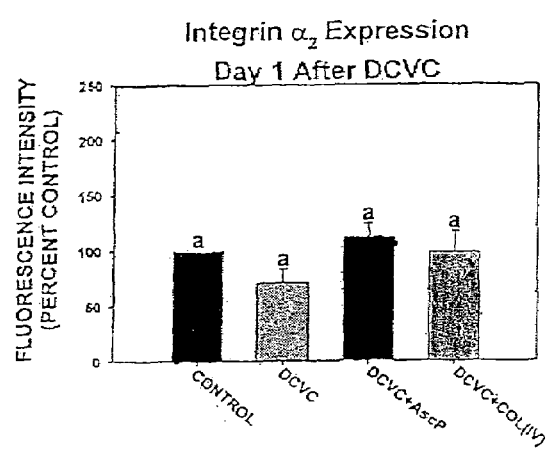
Figure 14D:
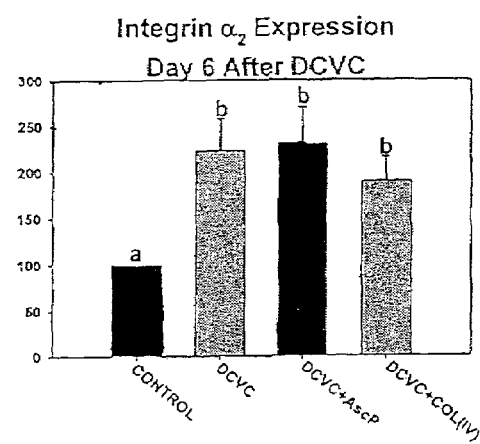
Figure 14E:
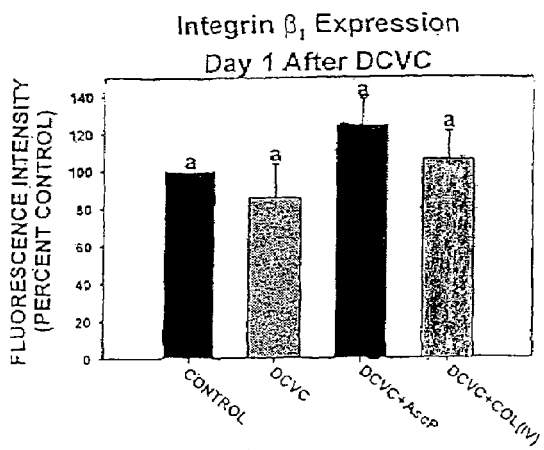
Figure 14F:
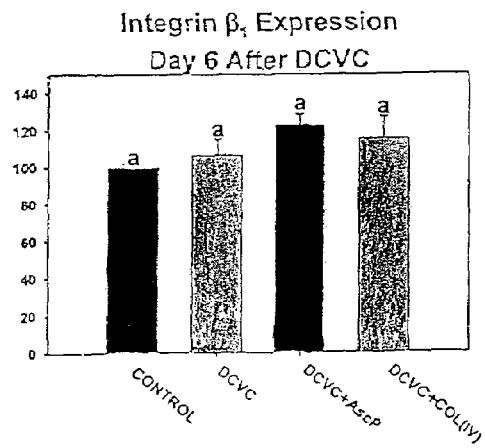

Effects of Sublethal Injury and Exogenous Collagen IV on Total CBI Expression in RPTC Monoclonal antibodies to the collagen-binding integrin subunits $\alpha_1$, $\alpha_2$, and $\beta_1$ and flow cytometry were used to measure total plasma membrane expression of collagen-binding integrins on days 1 and 6 following S-(1,2-dichlorovinyl)-L-cysteine exposure. FIG. 13 demonstrates the fluorescence shift observed in response to incubation of rabbit renal proximal tubular cells with the anti-integrin antibodies for individual CBI subunits. Exposure of uninjured renal proximal tubular cells to pharmacological concentrations of L-ascorbic acid-2-phosphate or exogenous collagen IV did not affect collagen-binding integrin. $\alpha_1$, $\alpha_2$, and $\beta_1$ expression. Following exposure to S-(1,2-dichlorovinyl)-L-cysteine, levels of expression of collagen-binding integrin subunits $\alpha_1$, $\alpha_2$, and $\beta_1$ in injured renal proximal tubular cells were unchanged on day 1 compared to controls (FIGS. 14A, 14C and 14E). On day 6 after injury, expression of collagen-binding integrin subunits $\alpha_1$ and $\beta_1$ were unchanged in DCVC-injured renal proximal tubular cells compared to controls (FIG. 14B and 14F). However, membrane expression of collagen-binding integrin subunit $\alpha_2$ was increased approximately 2.2 fold in S-(1,2-dichlorovinyl)-L-cysteine-injured renal proximal tubular cells (FIG. 14D). The presence of pharmacological concentrations of AscP or exogenous collagen IV did not affect the expression of collagen-binding integrin subunits $\alpha_1$, $\alpha_2$, or $\beta_1$ in sublethally injured renal proximal tubular cells.

EXAMPLE 27

Figure 15A:
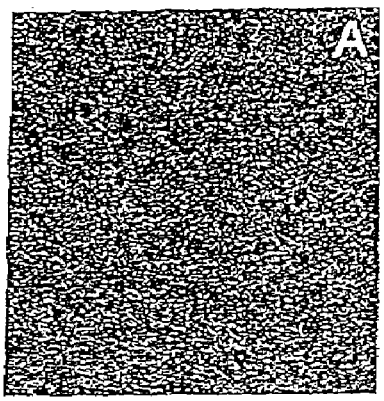
FIGS. 15A–15H show basal membrane localization of CBI subunit $\alpha_1$ in renal proximal tubular cells on day 1 (FIGS. 15A–15D) and day 6 (FIGS. 15E–15H) after S-(1,2-dichlorovinyl)-L-cysteine exposure.
Figure 15E:
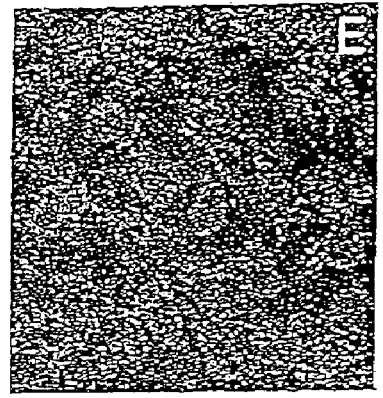
Figure 15B:
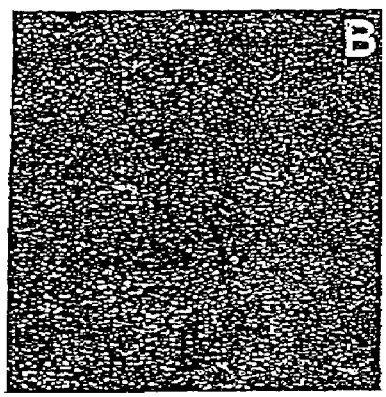
Figure 15F:
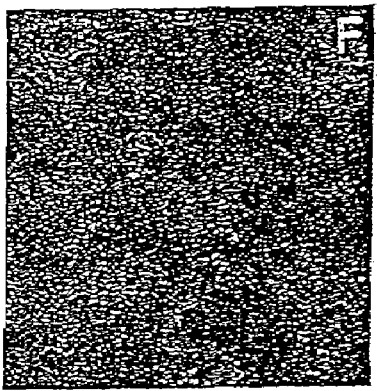
Figure 15C:
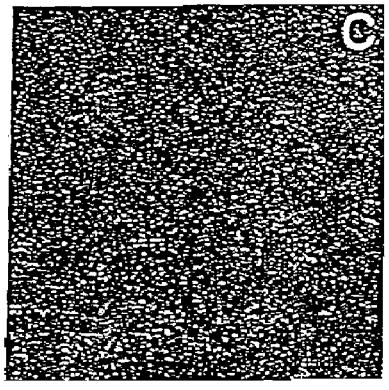
Figure 15G:
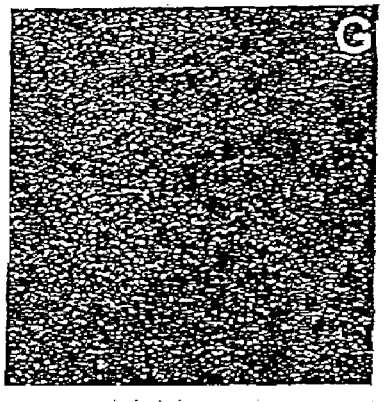
Figure 15D:
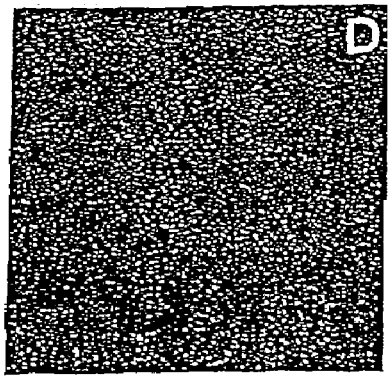
Figure 15H:
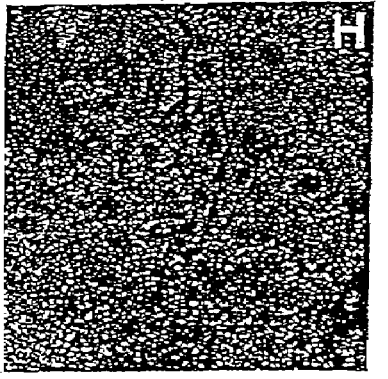
Figure 17A:
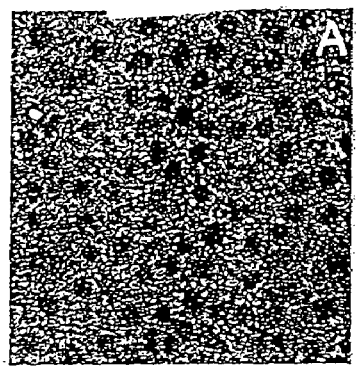
FIGS. 17A–17H show the basal membrane localization of CBI subunit $\alpha_2$ in renal proximal tubular cells on day 1 (FIGS. 17A–17D) and day 6 (FIGS. 17E–17H) after S-(1,2-dichlorovinyl)-L-cysteine exposure.
Figure 17E:
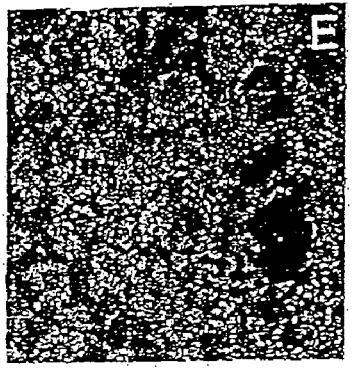
Figure 17B:
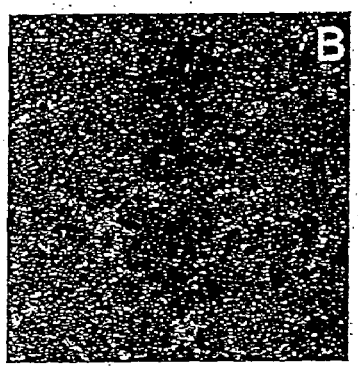
Figure 17F:
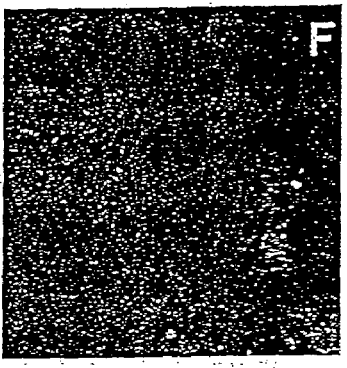
Figure 17C:
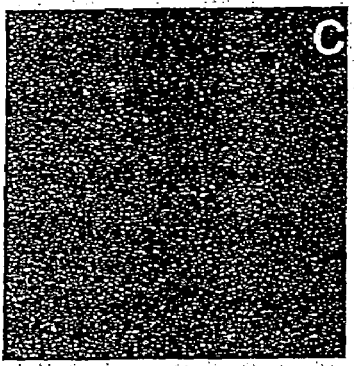
Figure 17G:
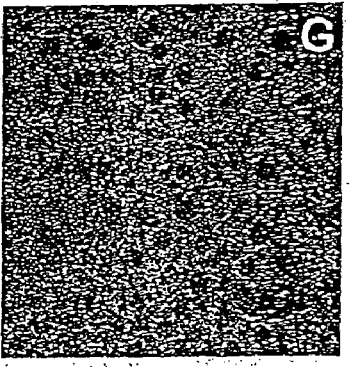
Figure 17D:
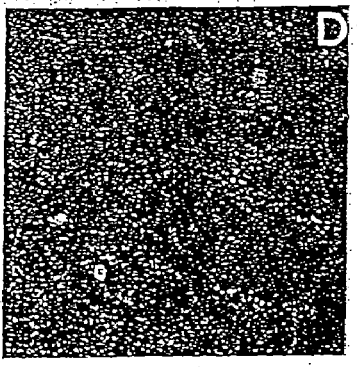
Figure 17H:
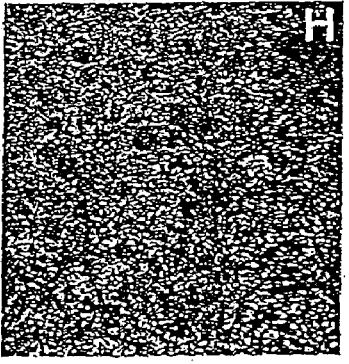
Figures 18A, 18B, 18C, 18D, 18E, 18F, 18G, 18H:
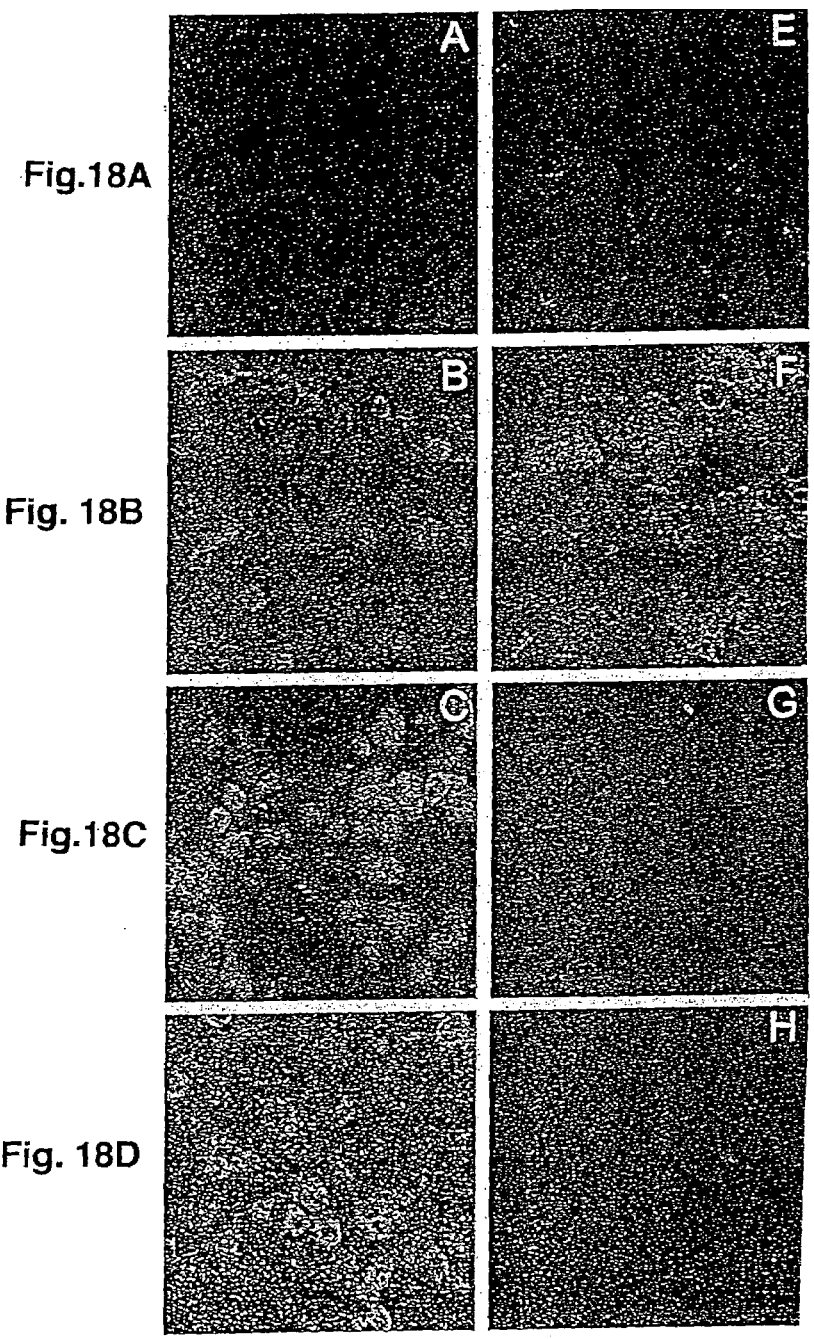
FIGS. 18A–18H show the apical membrane localization of CBI subunit $\beta_2$ in renal proximal tubular cells on day 1 (FIGS. 18A–18D) and day 6 (FIGS. 18E–18H) after S-(1,2-dichlorovinyl)-L-cysteine exposure.
Figure 19A:
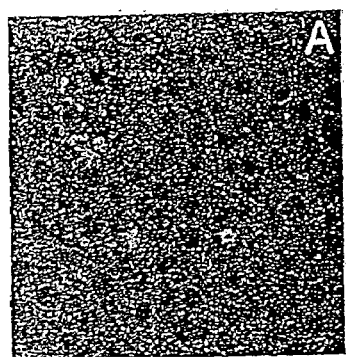
FIGS. 19A–19H show the basal membrane localization of CBI subunit $\beta_1$ in renal proximal tubular cells on day 1 (FIGS. 19A–19D) and day 6 (FIGS. 19E–19H) after S-(1,2-dichlorovinyl)-L-cysteine exposure.
Figure 19B:
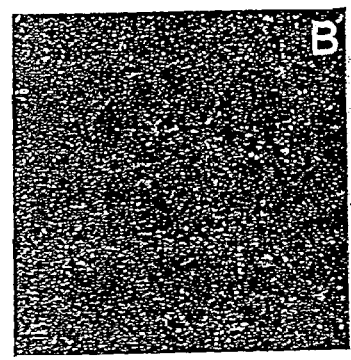
Figure 19C:
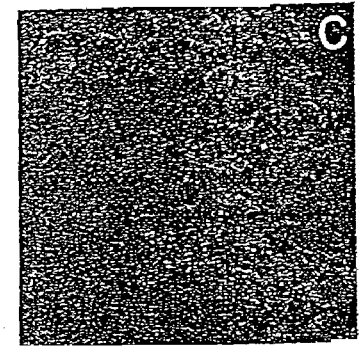
Figure 19D:
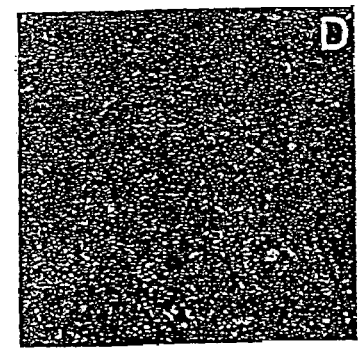
Figure 19E:
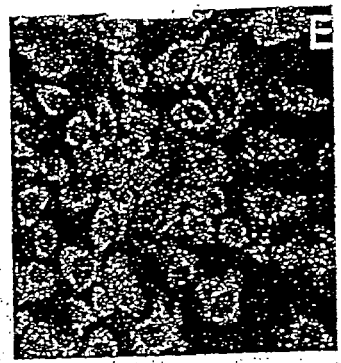
Figure 19F:
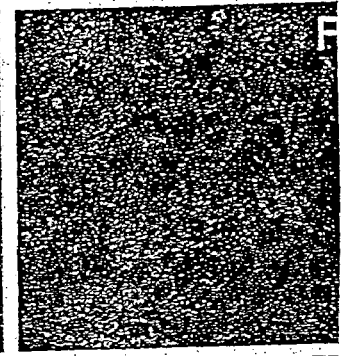
Figure 19G:
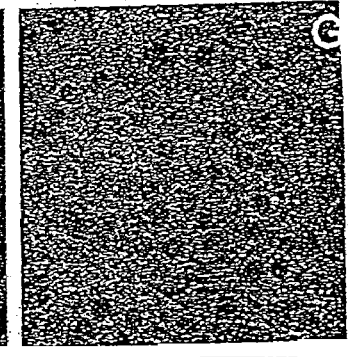
Figure 19H:
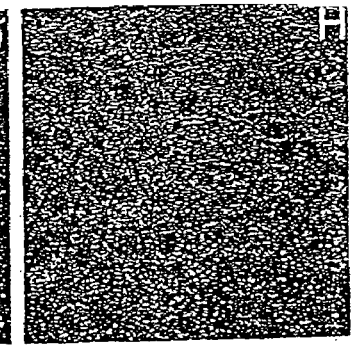

Effects of Sublethal Injury and Exogenous Collagen IV on the Subcellular Localization of Collagen-Binding Integrins in RPTC On day 1 following S-(1,2-dichlorovinyl)-L-cysteine exposure, the intensity of CBI $\alpha_1$, $\alpha_2$, and $\beta_1$ subunit fluorescent staining at the basal membrane was decreased compared to controls (FIGS. 15A–D 17A–D, and 19A–D). For comparison with injured renal proximal tubular cells on day 6, uninjured, sub-confluent (80%) renal proximal tubular cell cultures were used as controls for basal localization of CBI. As opposed to uninjured renal proximal tubular cells in day 12 of culture (6 days of growth to confluence plus the 6 experimentation days), sub-confluent renal proximal tubular cell cultures exhibit a morphology and cell density more like that of sublethally injured renal proximal tubular cell cultures. On day 6 after injury, basal localization of CBI subunits $\alpha_1$, $\alpha_2$, and $\beta_1$ in renal proximal tubular cells cultured in the absence of L-ascorbic acid-2-phosphate or exogenous collagen IV was still decreased compared to sub-confluent controls (FIGS. 15F, 17F, and 19F).

Figures 16A, 16B, 16C, 16D, 16E, 16F, 16G, 16H:
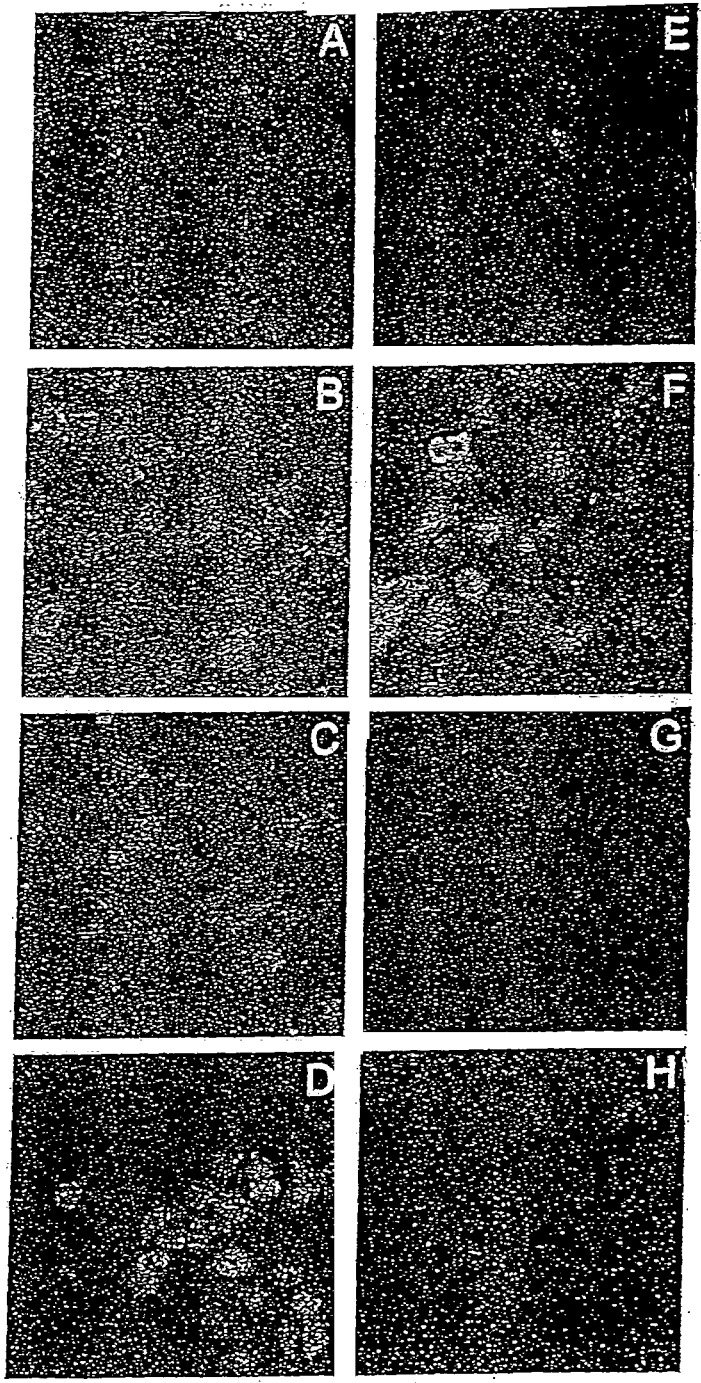
FIGS. 16A–16H show the apical membrane localization of CBI subunit $\alpha_1$ in renal proximal tubular cells on day 1
Figures 20A, 20B, 20C, 20D, 20E, 20F, 20G, 20H:
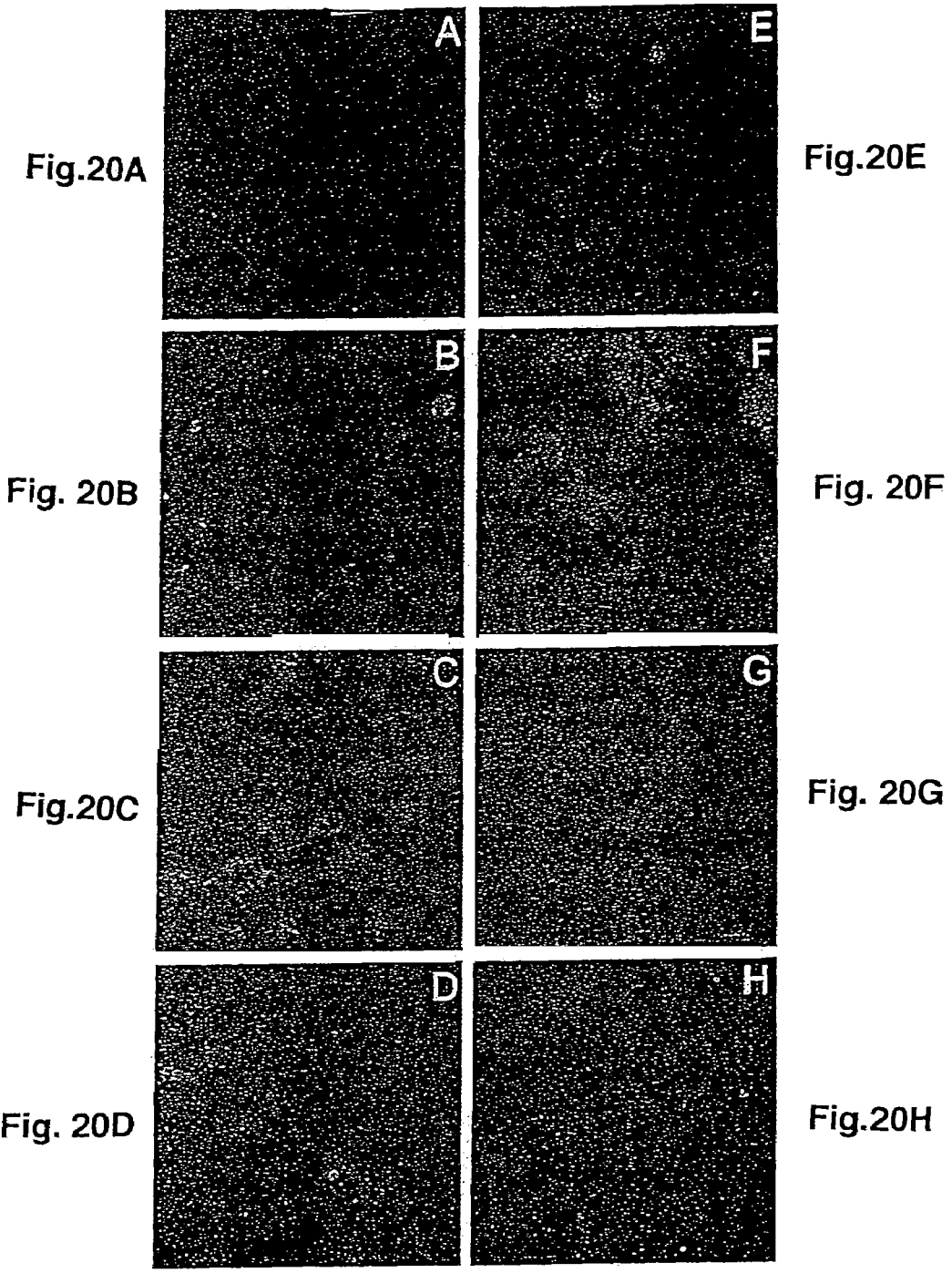
FIG. 20A–20H show the apical membrane localization of CBI subunit $\beta_1$ in renal proximal tubular cells on day 1 (FIGS. 20A–20D) and day 6 (FIGS. 20E–20H) after S-(1,2-dichlorovinyl)-L-cysteine exposure.

In contrast, sublethally injured renal proximal tubular cells cultured in the presence of either pharmacological concentrations of L-ascorbic acid-2-phosphate or exogenous collagen IV exhibited a return to control levels of basal localization of CBI subunits $\alpha_1$, $\alpha_2$, and $\beta_1$ (FIGS. 17G–H, 18G–H, and 19G–H). With respect to the apical membrane, uninjured controls showed no CBI staining, whereas CBI subunits $\alpha_1$, $\alpha_2$, and $\beta_1$ were partially redistributed to the apical membrane in sublethally injured renal proximal tubular cells on day 1 after injury (FIGS. 16A–D, 18A–D, and 20A–D). On day 6, sublethally injured renal proximal tubular cells continued to exhibit CBI is distributed to the apical membrane (FIGS. 16F, 18F, and 20F). However, injured renal proximal tubular cells cultured in the presence of pharmacological concentrations of AscP or exogenous collagen IV revealed a complete disappearance of OBIs from the apical membrane by day 6 (FIGS. 16G–H, 18G–H, and 20G–H). These data show that sustained redistribution of CBIs, characterized by a decreased basal localization and their appearance on the apical membrane of renal proximal tubular cells, is a consequence of sublethal injury by S-(1, 2-dichlorovinyl)-L-cysteine. In addition, sublethally injured renal proximal tubular cells cultured in the presence of pharmacological concentrations of L-ascorbic acid-2-phosphate or exogenous collagen IV are able to re-orient CBIs to the basal membrane.

EXAMPLE 28

Figure 21:
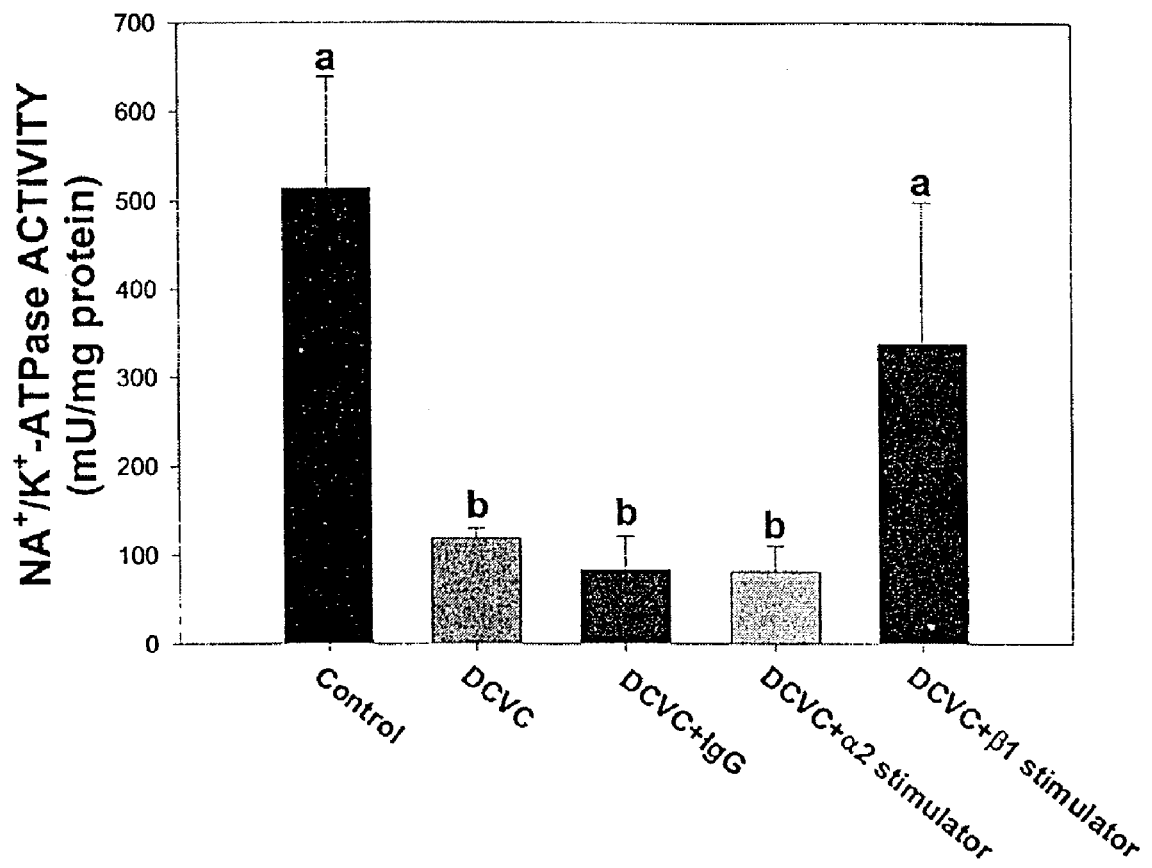
FIG. 21 shows $Na^+/K^+$-ATPase activity in renal proximal tubular cells sublethally injured by S-(1,2-dichlorovinyl)-L-cysteine and cultured in the absence or presence of function-stimulating antibodies to CBI subunits $\alpha_2$ or $\beta_1$ (5 μg/ml). $Na^+/K^+$-ATPase activity was measured on days 1 and 6 after injury. Data are presented as means±SEM, n=3–5 separate experiments. Bars labeled with different letter symbols are significantly different from each other (P<0.05).
Figure 22A:
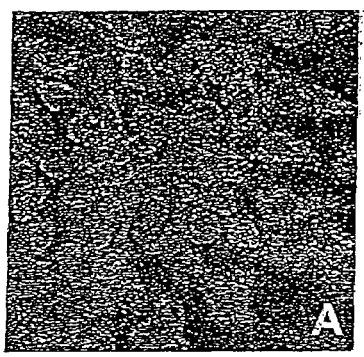
FIG. 22A–22F show basal (FIGS. 22A–22C) and apical (FIGS. 22D–22F) localization of CBI subunit $\beta_1$ on day 6 after S-(1,2-dichlorovinyl)-L-cysteine exposure in renal proximal tubular cells cultured in the absence or presence of CBI subunit $\beta_1$-stimulating antibodies.
Figure 22B:
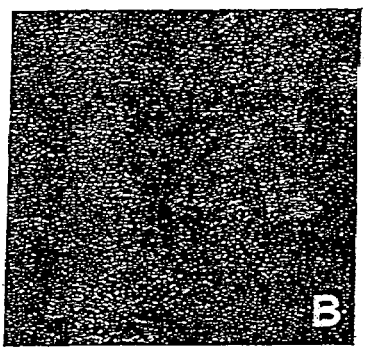
Figure 22C:
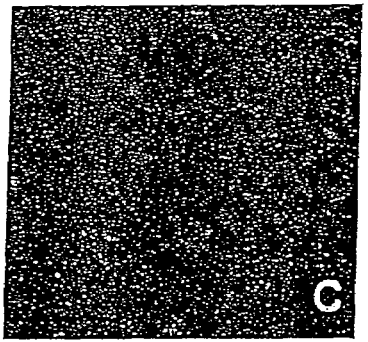
Figure 22D:
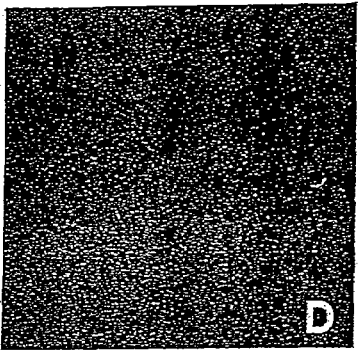
Figure 22E:
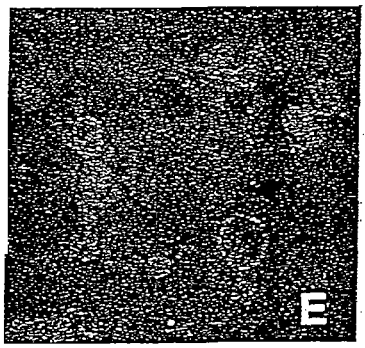
Figure 22F:
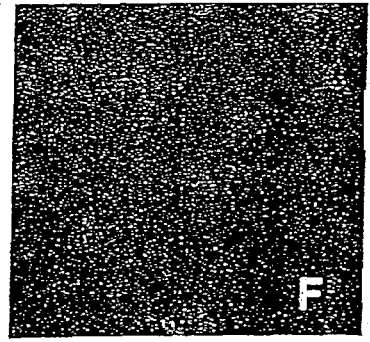

Effect of Function-Stimulating Antibodies to Collagen-Binding Integrins on $Na^+/K^+$-ATPase Activity and the Subcellular Localization of Collagen-Binding Integrins in RPTC Function-stimulating antibodies to CBI subunits $\alpha_2$ and $\beta_1$ were added to the culture media of S-(1,2-dichlorovinyl)-L-cysteine-injured renal proximal tubular cells. The function-stimulating antibodies did not affect the degree of S-(1,2-dichlorovinyl)-L-cysteine-induced renal proximal tubular cell injury on day 1 after exposure. On day 6 after injury, the /CBI $\beta_1$-stimulating antibody, but not the CBI $\alpha_2$-stimulating antibody, promoted the repair of $Na^+/K^+$-ATPase activity in S-(1,2-dichlorovinyl)-L-cysteine-injured renal proximal tubular cells (FIG. 21). The addition to the culture media of the antibodies to did not prevent basal delocalization or partial apical redistribution of CBIs $\alpha_2$ or $\beta_1$ on day 1 following DCVC exposure (data not shown). Despite the repair of $Na^+/K^+$-ATPase activity on day 6, CBI subunit $\beta_1$ remained delocalized and partially redistributed to the apical membrane in renal proximal tubular cells cultured in the presence of the $\beta_1$-stimulating antibody (FIG. 22).

Anchorage-dependent cell growth, proliferation, migration, and differentiation depend on the ability of the cell to recognize anchoring substrates in the extracellular matrix. Localization of ECM-binding integrins to the point of contact provides a strong but dynamic interaction that supports not only cellular attachment but also communication between the cell and the ECM. Given the importance of these interactions and the maintenance of cell polarity, the loss of integrin-extracellular matrix interactions and cell polarity play a key role in cell injury. Likewise, the restoration of integrin-extracellular matrix interactions and cell polarity likely play an equally important role in the return of normal cell function following injury.

Loss of renal epithelial cell polarity due to integrin distribution throughout the plasma membrane has been shown to b e a key event in renal dysfunction following acute chemical exposure or ischemia (Goligorsky and DiBona, 1993; Lieberthal et al., 1997; Molitoris and Marrs, 1999; Zuk et al., 1998). The resulting cellular disorientation and decreased renal tubular function is accompanied by sublethal injury, cell death and/or detachment from the tubular basement membrane (Frisch and Ruoslahti, 1997; Goligorsky and DiBona, 1993; Molitoris and Marrs, 1999; Tang et al., 1998). Despite the evidence demonstrating the loss of integrin polarity during renal cell injury, the importance of the restoration of integrin localization and cell polarity in tubular regeneration following injury is not well understood (Goligorsky and DiBona, 1993; Lieberthal et al., 1997; Kreidberg and Symons, 2000; Molitoris and Marrs, 1999; Zuk et al, 1998). As described above, the ability of injured renal proximal tubular cells to deposit collagen IV is associated with the repair of inhibited physiological functions following S-(1,2-dichlorovinyl)-L-cysteine injury. Further, exogenous collagen IV added to the culture media of injured renal proximal tubular cells promotes repair of physiological functions, providing the first evidence that a key extracellular matrix protein in the renal proximal tubule is involved in cell repair following injury. Because renal epithelial cells interact with collagen IV through CBIs, these data suggest that physiological repair in injured renal proximal tubular cells may involve an effect of collagen IV on the expression, localization, and/or function of CBIs. As mentioned above, sublethally injured cells may experience a loss in cell polarity due to decreased localization of certain proteins to specific areas of the plasma membrane.

Two potential reasons for a decrease in basal membrane protein localization include a decrease in membrane expression of these proteins due to translational effects or receptor internalization, or the redistribution of these proteins to other areas of the plasma membrane. Following S-(1,2-dichlorovinyl)-L-cysteine-induced sublethal injury to RPTC, no changes in total membrane expression of CBIs were evident on day 1. However, confocal microscopy showed that CBI localization to the basal membrane was decreased and accompanied by the appearance of CBIs on the apical membrane. These observations show that sublethal toxicant injury produces a decrease in basal CBI localization due to redistribution of CBIs as opposed to decreased overall expression of CBIs on the plasma membrane. On day 6 after injury, confocal microscopy demonstrated that all CBIs were still redistributed to the apical membrane, suggesting that S-(1,2-dichlorovinyl)-L-cysteine-injured renal proximal tubular cells remain disoriented with lost cellular polarity. These novel findings associate sustained integrin redistribution with the lack of repair of physiological functions following S-(1,2-dichlorovinyl)-L-cysteine injury.

Because pharmacological concentrations of AscP and exogenous collagen IV stimulated repair of physiological functions following S-(1,2-dichlorovinyl)-L-cysteine exposure, the effects of L-ascorbic acid-2-phosphate and exogenous collagen IV on the expression and localization of CBIs was determined. Addition of pharmacological concentrations of L-ascorbic acid-2-phosphate or exogenous collagen IV to culture media of injured renal proximal tubular cells produced no changes in total membrane expression of collagen binding integrins following sublethal injury. However, exposure to L-ascorbic acid-2-phosphate and exogenous collagen IV resulted in the return of basal membrane localization of collagen binding integrins with the loss of collagen binding integrins from the apical membrane. These observations suggest that the extracellular presence of collagen IV, whether stimulated by L-ascorbic acid-2-phosphate or added exogenously, promotes the return of cellular polarity characterized by the basal re-orientation of collagen binding integrins and the return of $Na^+/K^+$-ATPase activity. With regard to cell repair, these data suggest that an important step in the repair of physiological functions stimulated by extracellular collagen IV is the re-orientation of collagen binding integrins to the basal membrane and the restoration of cellular polarity.

On day 6 after S-(1,2-dichlorovinyl)-L-cysteine-injury, renal proximal tubular cells exhibited a significant increase in the membrane expression of CBI subunit $\alpha_2$ in the absence or presence of pharmacological concentrations of L-ascorbic acid-2-phosphate or exogenous collagen IV. The basal membrane localization of CBI subunit $\alpha_2$ on day 6 following injury correlated well with that of CBI subunits $\alpha_1$, and $\beta_1$, although membrane expression of those subunits did not change. Therefore, the physiological or pathological relevance of an increase in membrane expression of CBI subunit $\alpha_2$ in this study is not clear. However, the qualitative assessment of CBI localization used in this study allows for the comparison of spatially distinct membrane regions with regard to the absence or presence of CBIs. This method does not permit an accurate quantification of CBI density at the observed regions of the plasma membrane, nor does it account for CBIs localized to lateral membrane regions between the apical and basal membranes.

Because interactions between collagen IV and CBIs appeared to be associated with the promotion of physiological repair, repair may be stimulated by activating CBIs in the absence of collagen IV or L-ascorbic acid-2-phosphate. To test this hypothesis, injured renal proximal tubular cells were cultured in the presence of function-stimulating antibodies to CBI subunits $\alpha_2$ or $\beta_1$. Indeed, the CBI subunit $\beta_1$ antibody, but not the subunit $\alpha_2$ antibody, promoted the return of $Na^+/K^+$-ATPase activity in injured renal proximal tubular cells, suggesting that signaling through the $\beta_1$ integrin is linked to the repair of physiological functions. Despite the stimulation of repair, however, decreased CBI localization in the basal membrane and partial apical redistribution in injured renal proximal tubular cells were not reversed in response to treatment with the function-stimulating integrin antibodies. This result suggests that activation of $\beta_1$ integrins may promote repair through a mechanism that is independent of CBI relocalization following injury. This idea gains some support from knowledge of the signaling events surrounding ECM-integrin binding. Outside-in signaling cascades mediated by integrins usually begin with the phosphorylation of focal adhesion kinase (FAK), promoting the formation of focal adhesions around areas of integrin clustering (Burridge et al., 1992; Kornberg et al., 1992; Hauck et al., 2000). Collagen IV has been shown to stimulate ERK activation in a manner that requires FAK, demonstrating a signaling pathway initiated upon integrin-mediated attachment to collagen IV (Sanders and Basson, 2000). Other studies have demonstrated integrin-mediated ERK activation independent of FAK phosphorylation or through FAK effects on different pathways (Barberis et al., 2000; Lin et al., 1997). However, the relationship between ERK activation and repair of physiological functions is not known. Therefore, linking repair and the activation of $\beta_1$ independent of integrin-extracellular matrix interactions in renal proximal tubular cells requires further study.

Alternatively, the $\beta_1$ subunit can associate with any of at least eleven integrin subunits ($\alpha_1$–$\alpha_{10}$ and $\alpha_v$), each combination producing a heterodimeric integrin with unique binding and signaling properties. Therefore, repair stimulated by the $\beta_1$ antibody may link repair with an $\alpha$-$\beta$ subunit combination that forms a non-collagen-binding integrin, though association of $\beta_1$ with $\alpha_1$ cannot be ruled out at this time. Additionally, the $\alpha_2$-stimulating antibody could be ineffective at activating the $\beta_1$ subunit in rabbit renal proximal tubular cells.

In conclusion, these data show that the total expression of CBIs in sublethally injured renal proximal tubular cells is not altered on day 1 following injury, but that the basal membrane localization of CBIs is decreased in injured renal proximal tubular cells. This decrease in localization stems from the redistribution of CBI subunits $\alpha_1$, $\alpha_2$, and $\beta_1$ to the apical membrane. On day 6 after injury, S-(1,2-dichlorovinyl)-L-cysteine-treated renal proximal tubular cells that do not repair physiological functions still exhibit decreased basal membrane localization of CBIs, accompanied by the presence of CBIs on the apical membrane.

In contrast, the presence of pharmacological concentrations of L-ascorbic acid-2-phosphate or exogenous collagen IV in the culture media of S-(1,2-dichlorovinyl)-L-cysteine-injured renal proximal tubular cells promotes the repair of physiological functions. This effect is related to the disappearance of CBIs from the apical membrane and basal membrane re-orientation of CBIs by day 6 after injury. These novel findings suggest that there is a specific role for collagen IV to promote physiological repair, in part, through the restoration of CBI localization and cellular polarity, shedding new light on the mechanisms of renal cell repair following chemical-induced injury. However, the addition of function-stimulating antibodies to integrin subunit $\beta_1$, though promoting physiological repair, did not promote the relocalization of CBIs to the basal membrane. Though CBI relocalization may be involved in promotion of repair by AscP or exogenous collagen IV, this finding suggests that integrin activation alone, regardless of localization, may provide an alternate mechanism for the repair of certain physiological functions in injured renal proximal tubular cells.

The following references were cited herein:
1. Abbate, M. and Remuzzi, G. *Ren Fail* 18: 377–388, 1996.
2. Alcain, et al., *J Bioenerg Biomembr* 26: 393–398, 1994.
3. Bailey, et al., *FEBS Lett* 99: 361–366, 1979.
4. Cantley, L. G. *Am J Physiol Renal Fluid Electrolyte Physiol* 271: F1103–F1113, 1996.
5. Chojkier, et al., *Anal Biochem* 108: 385–393, 1980.
6. Davidson, et al., *J Biol Chem* 272: 345–352, 1997.
7. Denk, P. O. and Knorr, M. *Eur J Ophthalmol* 8: 37–41, 1998.
8. Dixit, S. N. *Connect Tissue Res* 14: 31–40, 1985.
9. Englard, S. and Seifter, S. *Ann Rev Nutr* 6: 365–406, 1986.
10. Geesin, et al., *J Invest Dermatol* 90: 420–424, 1988.
11. Ghohestani, et al., *J Biol Chem* 275: 16002–16006, 2000.
12. Gibbs, et al., *Connect Tissue Res* 40: 173–188, 1999.
13. Hata, R. I. and Senoo, H. *J Cell Physiol* 138: 8–16, 1989.
14. Houglum, et al., *Am. J Clin Nutr* 54:1141S–1143S, 1991.
15. Hudson, et al., *J Biol Chem* 268: 26033–26036, 1993.
16. Ivanov, et al., *Atherosclerosis* 140: 25–24, 1998.
17. Juva, et al., *Science* 152: 92–4, 1966.
18. Kao, et al., *J Biol Chem* 254: 2234–2243, 1979.
19. Kalluri, et al., *J Clin Invest* 99: 2470–2478, 1997.

20. Kalluri, R. and Cosgrove, D. *J Biol Chem* 275: 12719–12724, 2000.
21. Komsa-Penkova, et al., *Biochim Biophys Acta* 1297: 171–181, 1996.
22. Laemmli, U. K. *Nature* 227: 680–685, 1970.
23. Lash, et al., *J Pharmacol Exp Ther* 269: 374–383, 1994.
24. Levine, M. *N Engl J Med* 314: 892–902, 1986.
25. Linsenmayer, T. F. *Cell Biology of the Extracellular Matrix*. New York: Plenum Press, 1991, p. 5–37.
26. Lowry, et al., *J Biol Chem* 193: 265–275, 1951.
27. Martensson, et al., *Nephrol Dial Transplant* 10: 1637–1643, 1995.
28. Miller, E. J. *Biochem* 10:1652–1659, 1971.
29. Miner, J. H. *Kidney Int.* 56: 2016–2024, 1999.
30. Moore, et al., *Toxicol Environ Chem* 17: 153–162, 1988.
31. Muller, U. and Brandli, A. W. *J Cell Sci* 112: 3855–3867, 1999.
32. Murad, et al., *Proc Natl Acad Sci USA* 78: 2879–2882, 1981.
33. Murad, et al., *J Invest Derm* 81: 158–162, 1983.
34. Niki, et al., *Hepatology* 23: 1673–1681, 1996.
35. Nowak, et al., *Am J Physiol Cell Physiol* 269: C1317–C1325, 1995.
36. Nowak, et al., *Am J Physiol Cell Physiol* 271: C2072–C2080, 1996.
37. Nowak, et al., *Am J Physiol Renal Physiol* 274: F509–515, 1998.
38. Nowak, et al., *Am J Physiol Renal Physiol* 276: F228–F236, 1999.
39. Nowak, et al., *Toxicol Appl Pharmacol* 167: 37–45, 2000.
40. Peterkofsky, B. *Am J Clin Nutr* 54: 1135S-1140S, 1991.
41. Pinnell, S. *Yale J Biol Med* 58: 553–559, 1985.
42. Rosenbloom, et al., *J Biol Chem* 245:3361–3368, 1970.
43. Schmidt, et al., *FEBS Lett* 312: 174–178, 1992.
44. Schwartz, et al., *Am J Physiol Renal Fluid Electrolyte Physiol* 246: F845–F852, 1984.
45. Shapiro, et al., *Am J Clin Nutr* 54:1209S-1213S, 1991.
46. Sullivan, et al., *J Biol Chem* 269: 22500–22506, 1994.
47. Tschank, et al., *Arch Biochem Biophys* 261: 312–323, 1988.
48. Venezian, et al., *J Cell Physiol* 174; 331–341, 1996.
49. Walker, P. D. *Lab Invest* 70: 229–345, 1994.
50. Wewer, et al., *J Biol Chem* 258: 12654–12660, 1983.
51. Yamada, K. M. and Kennedy, D. W. *J Cell Biol* 80: 492–498, 1979.

Any patents or publications mentioned in this specification are indicative of the levels of those skilled in the art to which the invention pertains. Further, these patents and publications are incorporated by reference herein to the same extent as if each individual publication was specifically and individually indicated to be incorporated by reference.

One skilled in the art will appreciate readily that the present invention is well adapted to carry out the objects and obtain the ends and advantages mentioned, as well as those objects, ends and advantages inherent herein. The present examples, along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method of recovering a cellular function in a cell following injury, wherein said injury impairs deposition of collagen IV in the extracellular matrix, comprising the step of:
    contacting said cell with an amount of collagen IV which restores deposition of collagen IV in the extracellular matrix wherein said collagen IV is at a concentration of from about 0.01 mM to about 100 mM,
    and wherein said cellular function is selected from the group consisting of $Na^+/K^+$-ATPase activity, active $Na^+$ transport, basal oxygen consumption, and localization of collagen-binding integrins to the basal membrane.

2. The method of claim 1, wherein said cell comprises a renal epithelial cell.

3. The method of claim 1, wherein said injury is selected from the group consisting of ischemic injury, drug-induced injury and a toxicant-induced injury.

4. The method of claim 3, wherein said injury is selected from the group consisting of drug-induced intestine injury, toxicant-induced intestinal injury, ischemic reperfusion injury of the intestine, ischemic bowel disease, drug-induced liver injury, toxicant-induced liver injury, ischemic reperfusion injury of the liver, acute liver failure, drug-induced lung injury, toxicant-induced lung injury, ischemic reperfusion injury of the lung, acute lung failure, drug-induced heart injury, toxicant-induced heart injury, ischemic reperfusion injury of the heart, acute heart failure, drug-induced brain injury, toxicant-induced brain injury, ischemic reperfusion injury of the brain, stroke, drug-induced kidney injury, toxicant-induced kidney injury, ischemic reperfusion injury of the kidney, acute renal failure, drug-induced eye injury, toxicant-induced eye injury, ischemic reperfusion injury of the eye, chronic liver failure, chronic renal failure and vascular injury.

* * * * *